United States Patent [19]

Matsumoto et al.

[11] Patent Number: 5,691,272
[45] Date of Patent: Nov. 25, 1997

[54] CARBOXYLATE AND HEAT-SENSITIVE RECORDING MATERIAL USING SAME

[75] Inventors: Mansuke Matsumoto, Kawanishi; Nobuaki Sasaki, Souraku-gun; Bunji Sawano, Minamikawachi-gun; Kiyoharu Hasegawa, Yokohama; Kazuyoshi Kikkawa, Kamakura, all of Japan

[73] Assignees: Mitsui Toatsu Chemicals, Inc., Tokyo; Yamamoto Chemicals, Inc., Yao, both of Japan

[21] Appl. No.: 696,464

[22] Filed: Aug. 14, 1996

Related U.S. Application Data

[62] Division of Ser. No. 422,033, Apr. 14, 1995, Pat. No. 5,559,247.

[30] Foreign Application Priority Data

| Apr. 26, 1994 | [JP] | Japan | 6-088426 |
| Jun. 2, 1994 | [JP] | Japan | 6-121082 |
| Aug. 9, 1994 | [JP] | Japan | 6-187280 |
| Aug. 25, 1994 | [JP] | Japan | 6-200774 |

[51] Int. Cl.$^6$ ........................ B41M 5/30
[52] U.S. Cl. ............. 503/217; 503/201; 503/216
[58] Field of Search ............ 427/150–152; 503/201, 216, 217

[56] References Cited

U.S. PATENT DOCUMENTS 4,521,793 6/1985 Kabashima et al. ............ 503/201

*Primary Examiner*—Bruce H. Hess
*Attorney, Agent, or Firm*—Burns, Doane, Swecker & Mathis

[57] ABSTRACT

A heat-sensitive recording material which has a support and a heat-sensitive recording layer containing at least one carboxylate represented by the following formula (1) or (2)

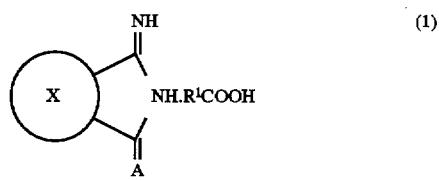

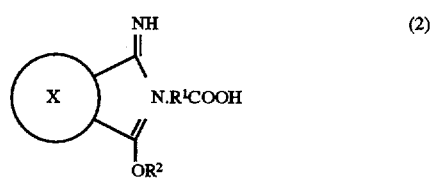

wherein a ring X is an aromatic residue which may have a substitute; the other substituents are as defined herein. The heat-sensitive recording material exhibits excellent color image stability and can provide an optically character-readable sharp image.

16 Claims, 6 Drawing Sheets

CARBOXYLATE AND HEAT-SENSITIVE RECORDING MATERIAL USING SAME

This application is a divisional of application Ser. No. 08/422,033, filed Apr. 14, 1995, now U.S. Pat. No. 5,559,247.

BACKGROUND OF THE INVENTION (i) Field of the Invention

The present invention relates to a novel carboxylate and a heat-sensitive recording material using the same. More specifically, the present invention relates to a heat-sensitive recording material which is excellent in the stability of a color image and which has absorptions in both the visible region and near infrared region.

(ii) Description of the Prior Art

In recent years, extensively prevalent heat-sensitive recording materials permit the easy formation of sharp color images by the use of a simple device, and for this reason, these recording materials have widely been put to practical use as papers for facsimiles and word processors, chart papers for various kinds of analyzers, tickets, commuter passes, prepaid cards, tags and the like. However, it is well known that these heat-sensitive recording materials, in which phthalide-based and fluoran-based leuco-pigments are used, have a problem that the stability of the color images is poor. In other words, these recording materials have a drawback that the color of the color images fades due to sunlight and the light of a fluorescent lamp, alcohol contained in cosmetics, a plasticizers contained in resin films or a plastic erasers, and the like.

Nowadays, the development of the facsimiles using plain papers has rapidly advanced, so that this field, in which the heat-sensitive recording papers have been most largely used, begins to be invaded. Therefore, the demand for the enhancement of the stability of the color images has been remarkably increased. Thus, in order to solve this problem, various investigations have been made.

One of these investigations is a trial that a metallic phthalocyanine is produced by a thermal reaction between a phthalocyanine precursor and a metallic salt. For example, in Japanese Patent Publication No. 8357/1983, 1-amino-3-iminoisoindolenine or its derivative and a metallic salt of an organic acid or a metal complex compound are used in a heat-sensitive layer. However, this heat-sensitive layer is poor in sensitivity, and there is also a problem that the metallic compound has a bad influence on the environment.

Furthermore, Japanese Patent Publication No. 16353/1992 discloses a recording material on which an imino compound such as 1,3-diiminoisoindoline is supported. However, it has been found that this diiminoisoindoline compound generates an ammonia gas in water to decompose into a phthalimide compound or an monoamide compound of an orthodicarboxylic acid. It has been understood that the diiminoisoindoline compound alone having 4 chlorine atoms in a benzene ring can be used for coating in an aqueous system, but the recording material using this compound has not developed any color, even when heat has been applied at 200° C. for 10 seconds.

Japanese Patent Publication Nos. 38995/1991 and 38996/1991 disclose heat-sensitive recording materials obtained by utilizing the reaction between an aromatic isocyanate and 1,3-diimino-4,5,6,7-tetrachloroisoindoline which does not decompose even when dispersed and coated in an aqueous system. These disclosed techniques have some defects, and for example, a color development sensitivity is still low, and the storage stability of the backgrounds of the heat-sensitive recording materials is also poor due to the aromatic isocyanate.

SUMMARY OF THE INVENTION

One object of the present invention is to provide a heat-sensitive recording material which is excellent in the stability of a color image and which has absorptions in both the visible region and the near infrared region.

Another object of the present invention is to provide a novel carboxylate.

The present inventors have intensively investigated to solve the above-mentioned problems, and as a result, the present invention has been completed. That is to say, the present invention is directed to a carboxylate represented by the following formula (1) or (2) and a heat-sensitive recording material in which the carboxylate is used:

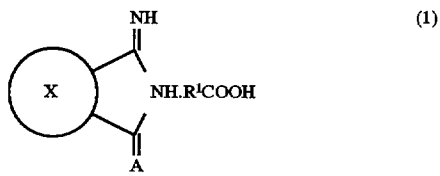

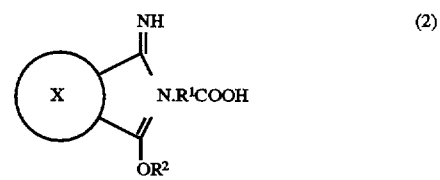

wherein a ring X is an aromatic residue which may have a substituent; A is =NH or —(OR$^3$ or OR$^4$)(wherein each of R$^3$ and R$^4$ is independently an alkyl group having 1 to 8 carbon atoms which may have a substituent, and R$^3$ and R$^4$ may bond to each other to form a ring); R$^1$ is a hydrogen atom, an alkyl group having 1 to 20 carbon atoms which may have a substituent, an aralkyl group which may have a substituent, or an aryl group which may have a substituent; and R$^2$ is an alkyl group having 1 to 8 carbon atoms which may have a substituent.

In this connection, if A in the formula (1) is =NH and R$^1$ is an aryl group which may have a substituent, the carboxylate is a novel compound.

The heat-sensitive recording material using this carboxylate can provide a sharp color image which is excellent in the stability of a color image and which is optically character-readable.

DETAILED DESCRIPTION OF THE PREFERRED EMBODIMENTS

Figure 1:
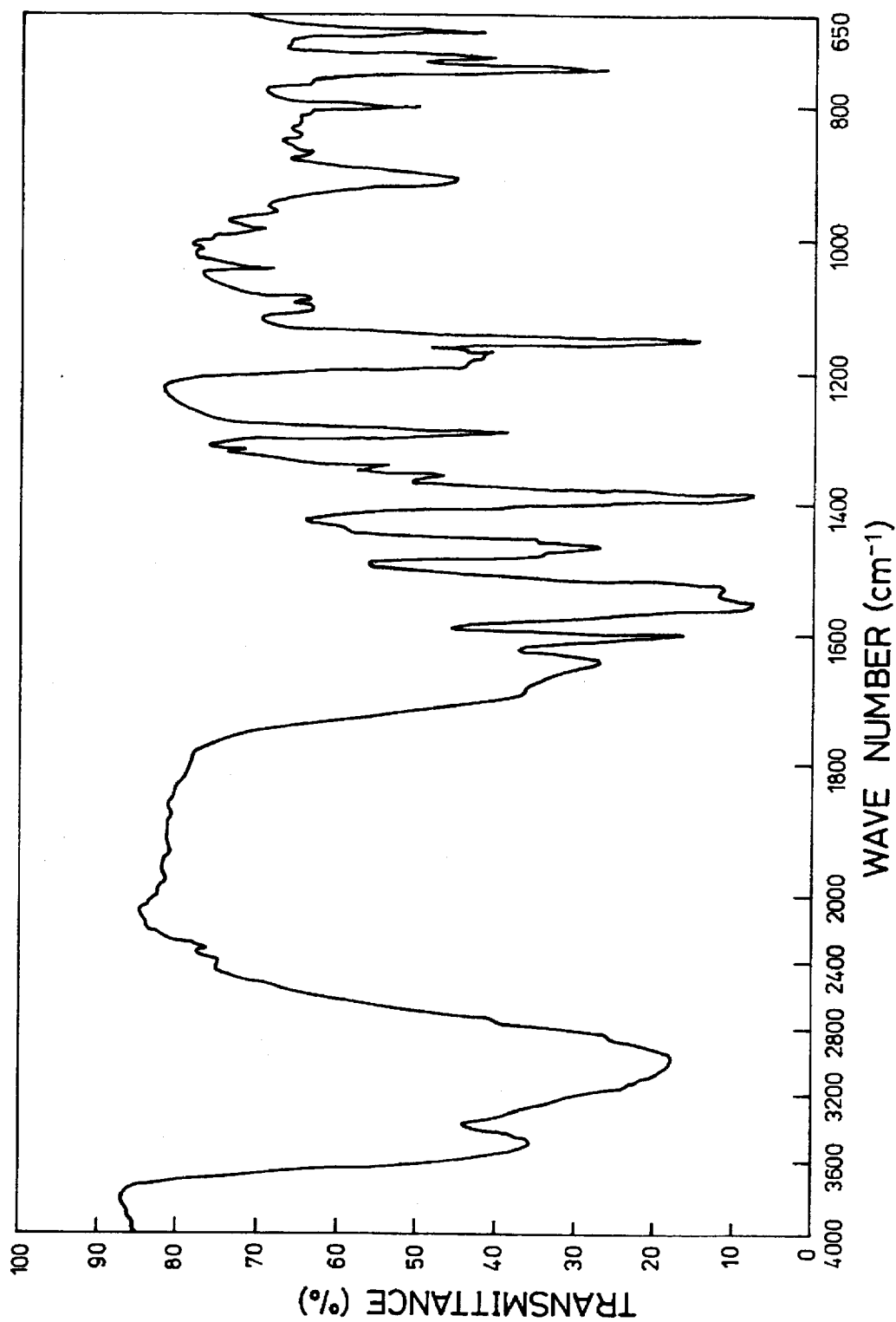
FIG. 1 shows the infrared absorption spectrum of a compound obtained in Example 1.

A carboxylate represented by the formula (1) can be prepared by reacting an imino compound represented by the formula (3) with a carboxylic acid represented by the formula (5) at 0° to 180° C. in the presence or absence of a solvent, and the carboxylate represented by the formula (2) can be prepared by reacting an imino compound represented by the formula (4) with the carboxylic acid represented by the formula ( 5) under the same conditions:

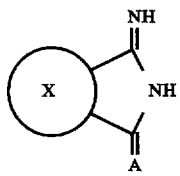

wherein the ring X and A are as defined in the formula (1),

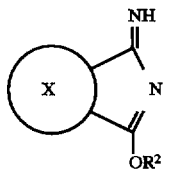

wherein the ring X and $R^2$ are as defined in the formula (2),

wherein $R^1$ is as defined in the formula (1) or (2).

The imino compound represented by the formula (3) or (4) is highly reactive, and it often reacts with an amino group, an imino group, an isocyanate group, a carbonyl group, a carboxyl group or a hydroxyl group by virtue of a small amount of heat to form a color former. Accordingly, the imino compound is considered to be a suitable compound as the color former for the heat-sensitive recording material. However, this imino compound reacts also with water to change to an inert imide compound, amide compound or carboxyl compound, so that it is impossible to coat a support with the imino compound in an aqueous system. In addition, the imino compound has a fatal defect. That is to say, even if the coating is made in an organic solvent system, the imino compound slowly decomposes by moisture in air and does not develop any color even when heat is applied (as an exceptional compound, there is 1,3-diimino-4,5,6,7-tetrachloroisoindoline which does not decompose in water, but this compound is extremely low in reactivity, and it does not develop any color by itself, even when heat of 200° C. is applied).

Investigations have been made to overcome this drawback, and as a result, it has been found that when an inorganic acid salt such as a hydrochloride, a sulfate, a nitrate, a chlorinate or a phosphate is used, a stable salt can be formed, but the formed salt is too stable, so that the desired reaction does not occur even if heat is applied. However, it has been discovered that a carboxylate can contribute to the production of an irreversible color former at the time of melting, while maintaining the stability to water. In this case, it has also been found that the carboxylate does not disturb the color development reaction of the imino compound. In addition, it has also been confirmed that most of the carboxylates have relatively low melting points and so they are suitable for the color development reaction at a low energy.

That is to say, the carboxylate of the present invention represented by the formula (1) or (2) has a performance which is perfect as a coloring component for the heat-sensitive recording material, i.e., a performance that the carboxylate is stable in an ordinary state but its reactivity promptly increases by the application of a small amount of heat.

The compound represented by the formula (1) or (2) is a salt produced by the reaction the imino compound represented by the formula (3) or (4) with a carboxylic acid represented by the formula (5):

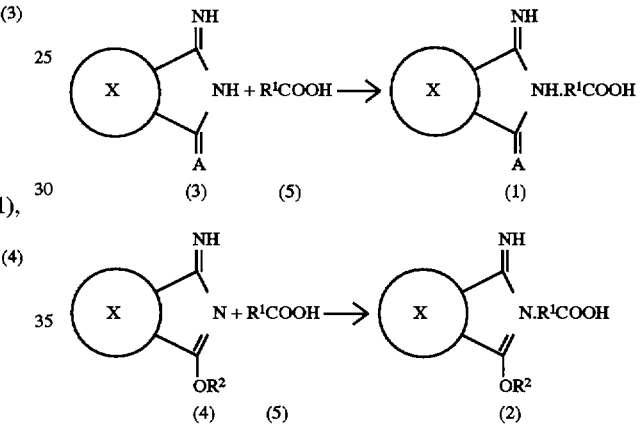

wherein a ring X, $R^1$, $R^2$ and A are as defined above.

The symbol "•" between the imino compound and the carboxylic acid in the formula (1) or (2) means that the salt is formed by both the compounds.

The molar ratio between the compound (3) or (4) and the compound (5) which can be used in the reaction is theoretically 1:1, but in fact, one or both the materials may be used in excess. However, in view of purification and the like after the reaction, it is preferable that the molar ratio is the compound (3) or (4):the compound (5)=1:0.2 to 1:5.

If either of the imino compound and the carboxylic acid is molten or dissolved, the reaction can proceed, and hence, under conditions of non-solvent, it is necessary to apply heat until either of the materials is molten.

The reaction temperature is preferably in the range of 0° to 180° C., more preferably 10° to 120° C., most preferably 20° to 70° C.

When the reaction is carried out in the dissolved state, a reaction solvent is used, and examples of the usable reaction solvent include alcohol solvents such as methanol, ethanol, isopropyl alcohol, n-butanol, n-amyl alcohol, n-hexyl alcohol, n-heptyl alcohol and n-octyl alcohol; aliphatic halogen solvents such as methylene chloride, chloroform, carbon tetrachloride, dichloroethane, trichloroethane, tetrachloroethane and tetrachloroethylene; and aromatic solvents such as benzene, toluene, xylene, chlorobenzene, dichlorobenzene and nitrobenzene.

The reaction time is the time necessary to melt or dissolve both the materials, because the reaction begins simultaneously when both of the compound (3) or (4) and the compound (5) are dissolved. In general, the reaction time is within 1 hour, but in some cases, several hours are required to form the desired salt.

In the case of the reaction in which the solvent is used, after the reaction has finished, the reaction system is cooled, and the resultant precipitate is collected by filtration and then dried to obtain a high-purity desired product. In the case of the non-solvent reaction, the desired product is obtained in the state of a solid mass, but in view of the purity of the product, the solid mass is preferably recrystallized from a suitable solvent. With regard to yield, when the imino compound (3) has no substituent, a high yield of 90% or more can often be obtained.

Examples of the usable substituent for the ring X of the imino compound represented by the formula (3) or (4) include halogen atoms, alkyl groups, alkoxy groups, aryloxy groups, alkylcarbonyl groups, arylcarbonyl groups, alkylthio groups, arylthio groups, a nitro group, dialkylamino groups, an amino group, alkylsilyl groups, alkylsilyloxy groups and a trifluoromethyl group.

Examples of the halogen atoms include fluorine, chlorine, bromine and iodine, and chlorine and iodine are preferable. Each alkyl moiety of the alkyl groups, the alkoxy groups, the alkylcarbonyl groups, the alkylthio groups, the dialkylamino groups, the alkylsilyl groups and the alkylsilyloxy groups is preferably an alkyl group having 1 to 12 carbon atoms, and each aryl moiety of the aryloxy groups, the arylcarbonyl groups and the arylthio groups is preferably a phenyl group, a naphthyl group or a biphenyl group.

Examples of the ring X include aromatic rings such as a benzene ring, a naphthalene ring, a biphenyl ring, an anthracene ring, an indene ring, a fluorene ring, a phenanthrene ring and an acenaphthene ring; and heterocyclic rings such as a furan ring, a pyrrole ring, a thiophene ring, a benzofuran ring, an indole ring, an indazole ring, a coumarone ring, a benzimidazolone ring, a benzothiophene ring, a benzoxazole ring, a benzothiazole ring, a benzimidazole ring, a pyridine ring, a quinoline ring, an isoquinoline ring, a quinazoline ring, an acridine ring, a phenazine ring, a pyrazine ring, an oxazine ring, a xanthene ring, a purine ring, a dibenzofuran ring and a dibenzopyrrole ring.

Typical examples of the imino compound represented by the formulae (3) and (4) include 1,3-diiminoisoindoline, 1,3-diimino-4-methylisoindoline, 1,3-diimino-5-methylisoindoline, 1,3-diimino-5-t-butylisoindoline, 1,3-diimino-5-t-amylisoindoline, 1,3-diimino-5-t-octylisoindoline, 1,3-diimino-4-chloroisoindoline, 1,3-diimino-5-chloroisoindoline, 1,3-diimino-4,5,6,7-tetrachloroisoindoline, 1,3-diimino-4,5,6,7-tetrabromoisoindoline, 1,3-diimino-4,5,6,7-tetrafluoroisoindoline, 1,3-diimino-4,7-dimethoxy-5,6-dichloroisoindoline, 1,3-diimino-4,7-diphenoxy-5,6-dichloroisoindoline, 1,3-diimino-4-methoxyisoindoline, 1,3-diimino-4-ethoxyisoindoline, 1,3-diimino-4-butoxyisoindoline, 1,3-diimino-4-hexyloxyisoindoline, 1,3-diimino-4-(2,5-dimethylpentyloxy)isoindoline, 1,3-diimino-5-butoxyisoindoline, 1,3-diimino-5-hexyloxyisoindoline, 1,3-diimino-5-(2,5-dimethylpentyloxy)isoindoline, 1,3-diimino-4-phenoxyisoindoline, 1,3-diimino-4-(4-t-butylphenoxy)isoindoline, 1,3-diimino-4-naphthyloxyisoindoline, 1,3-diimino-5-phenoxyisoindoline, 1,3-diimino-5-(4-t-butylphenoxy)-isoindoline, 1,3-diimino-5-naphthyloxyisoindoline, 1,3-diimino-4-ethylthioisoindoline, 1,3-diimino-4-butylthioisoindoline, 1,3-diimino-4-phenylthioisoindoline, 1,3-diimino-4-t-butylthioisoindoline, 1,3-diimino-5-ethylthioisoindoline, 1,3-diimino-5-butylthioisoindoline, 1,3-diimino-5-phenylthioisoindoline, 1,3-diimino-5-t-butylthioisoindoline, 1,3-diimino-4-dimethylaminoisoindoline, 1,3-diimino-4-diethylaminoisoindoline, 1,3-diimino-4-dibutylaminoisoindoline, 1,3-diimino-5-dimethylaminoisoindoline, 1,3-diimino-5-diethylaminoisoindoline, 1,3-diimino-5-dibutylaminoisoindoline, 1,3-diimino-4-aminoisoindoline, 1,3-diimino-5-aminoisoindoline, 1,3-diimino-4-nitroisoindoline, 1,3-diimino-5-nitroisoindoline, 1,3-diimino-4-dimethylsilylisoindoline, 1,3-diimino-4-diethylsilylisoindoline, 1,3-diimino-4-dibutylsilylisoindoline, 1,3-diimino-5-dimethylsilylisoindoline, 1,3-diimino-5-diethylsilylisoindoline, 1,3-diimino-5-dibutylsilylisoindoline, 1,3-diimino-4-dimethylsilyloxyisoindoline, 1,3-diimino-4-diethylsilyloxyisoindoline, 1,3-diimino-4-dibutylsilyloxyisoindoline, 1,3-diimino-5-dimethylsilyloxyisoindoline, 1,3-diimino-5-diethylsilyloxyisoindoline, 1,3-diimino-5-dibutylsilyloxyisoindoline, 1,3-diimino-4-trifluoromethyl-isoindoline, 1,3-diimino-5-trifluoromethylisoindoline, 3-iminoisoindoline, 3-imino-4,5,6,7-tetrachloroisoindoline, 3-imino-4,5,6,7-tetrabromoisoindoline, 3-imino-4,5,6,7-tetrafluoroisoindoline, 1,3-diiminobenzoisoindoline, 1,3-diimino-6-chlorobenzoisoindoline, 1,3-diimino-6-t-amylbenzoisoindoline, 1,3-diimino-6-nitrobenzoisoindoline, 1,3-diimino-6-aminobenzoisoindoline, 1,3-diimino-6-trimethylsilylbenzoisoindoline, 1,3-diimino-4,7-diazaisoindoline, 1,1-dimethoxy-3-iminoisoindoline, 1,1-diethoxy-3-iminoisoindoline, 1,1-di-n-propoxy-3-iminoisoindoline, 1,1-di-n-butoxy-3-iminoisoindoline, 1,1-di-n-amyloxy-3-iminoisoindoline, 1,1-di-n-hexyloxy-3-iminoisoindoline, 1,1-di-n-heptyloxy-3-iminoisoindoline, 1,1-di-n-octyloxy-3-iminoisoindoline, 1-methoxy-1-ethoxy-3-iminoisoindoline, 1-methoxy-1-n-propoxy-3-iminoisoindoline, 1-methoxy-1-n-butoxy-3-iminoisoindoline, 1-methoxy-1-n-amyloxy-3-iminoisoindoline, 1-methoxy-1-n-hexyloxy-3-iminoisoindoline, 1-methoxy-1-n-heptyloxy-3-iminoisoindoline, 1-methoxy-1-n-octyloxy-3-iminoisoindoline, 1-ethoxy-1-n-propoxy-3-iminoisoindoline, 1-ethoxy-1-n-butoxy-3-iminoisoindoline, 1-ethoxy-1-n-amyloxy-3-iminoisoindoline, 1-ethoxy-1-n-hexyloxy-3-iminoisoindoline, 1-ethoxy-1-n-heptyloxy-3-iminoisoindoline, 1-ethoxy-1-n-octyloxy-3-iminoisoindoline, 1-n-propoxy-1-n-butoxy-3-iminoisoindoline, 1,1-ethylenedioxy-3-iminoisoindoline, 1,1-(1'-methylethylenedioxy)-3-iminoisoindoline, 1,1-(1'-ethylethylenedioxy)-3-iminoisoindoline, 1,1-(1',2'-dimethylethylenedioxy)-3-iminoisoindoline, 1,1-(1'-n-propylethylenedioxy)-3-iminoisoindoline, 1,1-(1'-n-butyl-ethylenedioxy)-3-iminoisoindoline, 1,1-(1'-allyloxymethyl-ethylenedioxy)-3-iminoisoindoline, 1,1-(1'-hydroxymethyl-ethylenedioxy)-3-iminoisoindoline, 1,1-(1'-methoxymethyl-ethylenedioxy)-3-iminoisoindoline, 1,1-trimethylenedioxy-3-iminoisoindoline, 1,1-(1'-methyltrimethylenedioxy)-3-iminoisoindoline, 1,1-(2'-methyl-2'-ethyltrimethylene-dioxy)-3-iminoisoindoline, 1,1-(1',1',3'-trimethyltri-methylenedioxy)-3-iminoisoindoline, 1,1-dimethoxy-3-imino-4-chloroisoindoline, 1,1-dimethoxy-3-imino-5-chloroisoindoline, 1,1-dimethoxy-3-imino-6-chloroisoindoline, 1,1-dimethoxy-3-imino-7- chloroisoindoline, 1,1-dimethoxy-3-imino-4-methylisoindoline, 1,1-dimethoxy-3-imino-5-methylisoindoline, 1,1-dimethoxy-3-imino-6-methylisoindoline, 1,1-di-methoxy-3-imino-7-methylisoindoline, 1,1-dimethoxy-3-imino-4-t-butylisoindoline, 1,1-dimethoxy-3-imino-5-t-butylisoindoline, 1,1-dimethoxy-3-imino-6-t-butylisoindoline, 1,1-dimethoxy-3-imino-7-t-butylisoindoline, 1,1-dimethoxy-3-imino-4-methoxyisoindoline, 1,1-dimethoxy-3-imino-5-methoxyisoindoline, 1,1-dimethoxy-3-imino-6-methoxyisoindoline, 1,1-dimethoxy-3-imino-7-methoxyisoindoline, 1,1-dimethoxy-3-imino-4-ethoxyisoindoline, 1,1-dimethoxy-3-imino-5-ethoxyisoindoline, 1,1-dimethoxy-3-imino-6-ethoxyisoindoline, 1,1-dimethoxy-3-imino-7-ethoxyisoindoline, 1,1-dimethoxy-3-imino-4-n-propoxyisoindoline, 1,1-dimethoxy-3-imino-5-n-propoxyisoindoline, 1,1-dimethoxy-3-imino-6-n-propoxyisoindoline, 1,1-dimethoxy-3-imino-7-n-propoxyisoindoline, 1,1-dimethoxy-3-imino-4-n-butoxyisoindoline, 1,1-dimethoxy-3-imino-5-n-butoxyisoindoline, 1,1-dimethoxy-3-imino-6-n-butoxyisoindoline, 1,1-dimethoxy-3-imino-7-n-butoxyisoindoline, 1,1-dimethoxy-3-imino-4-n-hexyloxyisoindoline, 1,1-dimethoxy-3-imino-5-n-hexyloxy-isoindoline, 1,1-dimethoxy-3-imino-6-n-hexyloxyisoindoline, 1,1-dimethoxy-3-imino-7-n-hexyloxyisoindoline, 1,1-dimethoxy-3-imino-4-(2',4'-dimethylpentyloxy)isoindoline, 1,1-dimethoxy-3-imino-5-(2',4'-dimethylpentyl-oxy)isoindoline, 1,1-dimethoxy-3-imino-6-(2',4'-dimethylpentyloxy)isoindoline, 1,1-dimethoxy-3-imino-7-(2',4'-dimethylpentyloxy)isoindoline, 1,1-dimethoxy-3-imino-4-n-octyloxyisoindoline, 1,1-dimethoxy-3-imino-5-n-octyloxyisoindoline, 1,1-dimethoxy-3-imino-6-n-octyloxyisoindoline, 1,1-dimethoxy-3-imino-7-n-octyloxyisoindoline, 1,1-dimethoxy-3-imino-4-phenoxyisoindoline, 1,1-dimethoxy-3-imino-5-phenoxyisoindoline, 1,1-dimethoxy-3-imino-6-phenoxyisoindoline, 1,1-dimethoxy-3-imino-7-phenoxyisoindoline, 1,1-dimethoxy-3-imino-4-(4'-t-butylphenylthio)isoindoline, 1,1-dimethoxy-3-imino-5-(4'-t-butylphenylthio)isoindoline, 1,1-dimethoxy-3-imino-6-(4'-t-butylphenylthio)isoindoline, 1,1-dimethoxy-3-imino-7-(4'-t-butylphenylthio)isoindoline, 1,1-dimethoxy-3-imino-4-nitroisoindoline, 1,1-dimethoxy-3-imino-5-nitroisoindoline, 1,1-dimethoxy-3-imino-6-nitroisoindoline, 1,1-dimethoxy-3-imino-7-nitroisoindoline, 1,1-dimethoxy-3-imino-4-diethylaminoisoindoline, 1,1-dimethoxy-3-imino-5-diethylaminoisoindoline, 1,1-dimethoxy-3-imino-6-diethylaminoisoindoline, 1,1-dimethoxy-3-imino-7-diethylaminoisoindoline, 1,1-diethoxy-3-imino-4-chloroisoindoline, 1,1-diethoxy-3-imino-5-chloroisoindoline, 1,1-diethoxy-3-imino-6-chloroisoindoline, 1,1-diethoxy-3-imino-7-chloroisoindoline, 1,1-diethoxy-3-imino-4-methylisoindoline, 1,1-diethoxy-3-imino-5-methylisoindoline, 1,1-diethoxy-3-imino-6-methylisoindoline, 1,1-diethoxy-3-imino-7-methylisoindoline, 1,1-diethoxy-3-imino-4-t-butylisoindoline, 1,1-diethoxy-3-imino-5-t-butylisoindoline, 1,1-diethoxy-3-imino-6-t-butylisoindoline, 1,1-diethoxy-3-imino-7-t-butylisoindoline, 1,1-diethoxy-3-imino-4-methoxyisoindoline, 1,1-diethoxy-3-imino-5-methoxyisoindoline, 1,1-diethoxy-3-imino-6-methoxyisoindoline, 1,1-diethoxy-3-imino-7-methoxyisoindoline, 1,1-diethoxy-3-imino-4-ethoxyisoindoline, 1,1-diethoxy-3-imino-5-ethoxyisoindoline, 1,1-diethoxy-3-imino-6-ethoxyisoindoline, 1,1-diethoxy-3-imino-7-ethoxyisoindoline, 1,1-diethoxy-3-imino-4-n-propoxyisoindoline, 1,1-diethoxy-3-imino-5-n-propoxyisoindoline, 1,1-diethoxy-3-imino-6-n-propoxyisoindoline, 1,1-diethoxy-3-imino-7-n-propoxyisoindoline, 1,1-diethoxy-3-imino-4-n-butoxyisoindoline, 1,1-diethoxy-3-imino-5-n-butoxyisoindoline, 1,1-diethoxy-3-imino-6-n-butoxyisoindoline, 1,1-diethoxy-3-imino-7-n-butoxyisoindoline, 1,1-diethoxy-3-imino-4-n-hexyloxyisoindoline, 1,1-diethoxy-3-imino-5-n-hexyloxyisoindoline, 1,1-diethoxy-3-imino-6-n-hexyloxyisoindoline, 1,1-diethoxy-3-imino-7-n-hexyloxyisoindoline, 1,1-diethoxy-3-imino-4-(2',4'-dimethylpentyloxy)isoindoline, 1,1-diethoxy-3-imino-5-(2',4'-dimethylpentyloxy)isoindoline, 1,1-diethoxy-3-imino-6-(2',4'-dimethylpentyloxy)isoindoline, 1,1-diethoxy-3-imino-7-(2',4'-dimethylpentyloxy)isoindoline, 1,1-diethoxy-3-imino-4-n-octyloxyisoindoline, 1,1-diethoxy-3-imino-5-n-octyloxyisoindoline, 1,1-diethoxy-3-imino-6-n-octyloxyisoindoline, 1,1-diethoxy-3-imino-7-n-octyloxyisoindoline, 1,1-diethoxy-3-imino-4-phenoxyisoindoline, 1,1-diethoxy-3-imino-5-phenoxyisoindoline, 1,1-diethoxy-3-imino-6-phenoxyisoindoline, 1,1-diethoxy-3-imino-7-phenoxyisoindoline, 1,1-diethoxy-3-imino-4-(4'-t-butylphenylthio)isoindoline, 1,1-diethoxy-3-imino-5-(4'-t-butylphenylthio)isoindoline, 1,1-diethoxy-3-imino-6-(4'-t-butylphenylthio)isoindoline, 1,1-diethoxy-3-imino-7-(4'-t-butylphenylthio)isoindoline, 1,1-diethoxy-3-imino-4-nitroisoindoline, 1,1-diethoxy-3-imino-5-nitroisoindoline, 1,1-diethoxy-3-imino-6-nitroisoindoline, 1,1-diethoxy-3-imino-7-nitroisoindoline, 1,1-diethoxy-3-imino-4-diethylaminoisoindoline, 1,1-diethoxy-3-imino-5-diethylaminoisoindoline, 1,1-diethoxy-3-imino-6-diethylaminoisoindoline, 1,1-diethoxy-3-imino-7-diethylaminoisoindoline, 1,1-ethylenedioxy-3-imino-4-chloroisoindoline, 1,1-ethylenedioxy-3-imino-5-chloroisoindoline, 1,1-ethylenedioxy-3-imino-6-chloroisoindoline, 1,1-ethylenedioxy-3-imino-7-chloroisoindoline, 1,1-ethylenedioxy-3-imino-4-methylisoindoline, 1,1-ethylenedioxy-3-imino-5-methylisoindoline, 1,1-ethylenedioxy-3-imino-6-methylisoindoline, 1,1-ethylenedioxy-3-imino-7-methylisoindoline, 1,1-ethylenedioxy-3-imino-4-t-butylisoindoline, 1,1-ethylenedioxy-3-imino-5-t-butylisoindoline, 1,1-ethylenedioxy-3-imino-6-t-butylisoindoline, 1,1-ethylenedioxy-3-imino-7-t-butylisoindoline, 1,1-ethylenedioxy-3-imino-4-methoxyisoindoline, 1,1-ethylenedioxy-3-imino-5-methoxyisoindoline, 1,1-ethylenedioxy-3-imino-6-methoxyisoindoline, 1,1-ethylenedioxy-3-imino-7-methoxyisoindoline, 1,1-ethylenedioxy-3-imino-4-ethoxyisoindoline, 1,1-ethylenedioxy-3-imino-5-ethoxyisoindoline, 1,1-ethylenedioxy-3-imino-6-ethoxyisoindoline, 1,1-ethylenedioxy-3-imino-7-ethoxyisoindoline, 1,1-ethylenedioxy-3-imino-4-n-propoxyisoindoline, 1,1-ethylenedioxy-3-imino-5-n-propoxyisoindoline, 1,1-ethylenedioxy-3-imino-6-n-propoxyisoindoline, 1,1-ethylenedioxy-3-imino-7-n-propoxyisoindoline, 1,1-ethylenedioxy-3-imino-4-n-butoxyisoindoline, 1,1-ethylenedioxy-3-imino-5-n-butoxyisoindoline, 1,1-ethylenedioxy-3-imino-6-n-butoxyisoindoline, 1,1-ethylenedioxy-3-imino-7-n-butoxyisoindoline, 1,1-ethylenedioxy-3-imino-4-n- hexyloxyisoindoline, 1,1-ethylenedioxy-3-imino-5-n-hexyloxyisoindoline, 1,1-ethylenedioxy-3-imino-6-n-hexyloxyisoindoline, 1,1-ethylenedioxy-3-imino-7-n-hexyloxyisoindoline, 1,1-ethylenedioxy-3-imino-4-(2',4'-dimethylpentyloxy)isoindoline, 1,1-ethylenedioxy-3-imino-5-(2',4'-dimethylpentyloxy)isoindoline, 1,1-ethylenedioxy-3-imino-6-(2',4'-dimethylpentyloxy)isoindoline, 1,1-ethylenedioxy-3-imino-7-(2',4'-dimethylpentyloxy)isoindoline, 1,1-ethylenedioxy-3-imino-4-n-octyloxyisoindoline, 1,1-ethylenedioxy-3-imino-6-n-octyloxyisoindoline, 1,1-ethylenedioxy-3-imino-4-n-octyloxyisoindoline, 1,1-ethylenedioxy-3-imino-7-n-octyloxyisoindoline, 1,1-ethylenedioxy-3-imino-4-phenoxyisoindoline, 1,1-ethylenedioxy-3-imino-5-phenoxyisoindoline, 1,1-ethylenedioxy-3-imino-6-phenoxyisoindoline, 1,1-ethylenedioxy-3-imino-7-phenoxyisoindoline, 1,1-ethylenedioxy-3-imino-4-(4'-t-butylphenylthio)isoindoline, 1,1-ethylenedioxy-3-imino-5-(4'-t-(4-t-butylphenylthio)isoindoline, 1,1-ethylenedioxy-3-imino-6-(4'-t-butylphenylthio)isoindoline, 1,1-ethylenedioxy-3-imino-7-(4'-t-butylphenylthio)isoindoline, 1,1-ethylenedioxy-3-imino-4-nitroisoindoline, 1,1-ethylenedioxy-3-imino-5-nitroisoindoline, 1,1-ethylenedioxy-3-imino-6-nitroisoindoline, 1,1-ethylenedioxy-3-imino-7-nitroisoindoline, 1,1-ethylenedioxy-3-imino-4-diethylaminoisoindoline, 1,1-ethylenedioxy-3-imino-5-diethylaminoisoindoline, 1,1-ethylenedioxy-3-imino-6-diethylaminoisoindoline, 1,1-ethylenedioxy-3-imino-7-diethylaminoisoindoline, 1,1-trimethylenedioxy-3-imino-4-chloroisoindoline, 1,1-trimethylenedioxy-3-imino-5-chloroisoindoline, 1,1-trimethylenedioxy-3-imino-6-chloroisoindoline, 1,1-trimethylenedioxy-3-imino-7-chloroisoindoline, 1,1-trimethylenedioxy-3-imino-4-methylisoindoline, 1,1-trimethylenedioxy-3-imino-5-methylisoindoline, 1,1-trimethylenedioxy-3-imino-6-methylisoindoline, 1,1-trimethylenedioxy-3-imino-7-methylisoindoline, 1,1-trimethylenedioxy-3-imino-4-t-butylisoindoline, 1,1-trimethylenedioxy-3-imino-5-t-butylisoindoline, 1,1-trimethylenedioxy-3-imino-6-t-butylisoindoline, 1,1-trimethylenedioxy-3-imino-7-t-butylisoindoline, 1,1-trimethylenedioxy-3-imino-4-methoxyisoindoline, 1,1-trimethylenedioxy-3-imino-5-methoxyisoindoline, 1,1-trimethylenedioxy-3-imino-6-methoxyisoindoline, 1,1-trimethylenedioxy-3-imino-7-methoxyisoindoline, 1,1-trimethylenedioxy-3-imino-4-ethoxyisoindoline, 1,1-trimethylenedioxy-3-imino-5-ethoxyisoindoline, 1,1-trimethylenedioxy-3-imino-6-ethoxyisoindoline, 1,1-trimethylenedioxy-3-imino-7-ethoxyisoindoline, 1,1-trimethylenedioxy-3-imino-4-n-propoxyisoindoline, 1,1-trimethylenedioxy-3-imino-5-n-propoxyisoindoline, 1,1-trimethylenedioxy-3-imino-6-n-propoxyisoindoline, 1,1-trimethylenedioxy-3-imino-7-n-propoxyisoindoline, 1,1-trimethylenedioxy-3-imino-4-n-butoxyisoindoline, 1,1-trimethylenedioxy-3-imino-5-n-butoxyisoindoline, 1,1-trimethylenedioxy-3-imino-6-n-butoxyisoindoline, 1,1-trimethylenedioxy-3-imino-7-n-butoxyisoindoline, 1,1-trimethylenedioxy-3-imino-4-n-hexyloxyisoindoline, 1,1-trimethylenedioxy-3-imino-5-n-hexyloxyisoindoline, 1,1-trimethylenedioxy-3-imino-6-n-hexyloxyisoindoline, 1,1-trimethylenedioxy-3-imino-7-n-hexyloxyisoindoline, 1,1-trimethylenedioxy-3-imino-4-(2',4'-dimethylpentyloxy)isoindoline, 1,1-trimethylenedioxy-3-imino-5-(2',4'-dimethylpentyloxy)isoindoline, 1,1-trimethylenedioxy-3-imino-6-(2',4'-dimethylpentyloxy)isoindoline, 1,1-trimethylenedioxy-3-imino-7-(2',4'-dimethylpentyloxy)isoindoline, 1,1-trimethylenedioxy-3-imino-4-n-octyloxyisoindoline, 1,1-trimethylenedioxy-3-imino-5-n-octyloxyisoindoline, 1,1-trimethylenedioxy-3-imino-6-n-octyloxyisoindoline, 1,1-trimethylenedioxy-3-imino-7-n-octyloxyisoindoline, 1,1-trimethylenedioxy-3-imino-4-octyloxyisoindoline, 1,1-trimethylenedioxy-3-imino-4-phenoxyisoindoline, 1,1-trimethylenedioxy-3-imino-5-phenoxyisoindoline, 1,1-trimethylenedioxy-3-imino-6-phenoxyisoindoline, 1,1-trimethylenedioxy-3-imino-7-phenoxyisoindoline, 1,1-trimethylenedioxy-3-imino-4-(4'-t-butylphenylthio)isoindoline, 1,1-trimethylenedioxy-3-imino-5-(4'-t-butylphenylthio)isoindoline, 1,1-trimethylenedioxy-3-imino-6-(4'-t-butylphenylthio)isoindoline, 1,1-trimethylenedioxy-3-imino-7-(4'-t-butylphenylthio)isoindoline, 1,1-trimethylenedioxy-3-imino-4-nitroisoindoline, 1,1-trimethylenedioxy-3-imino-5-nitroisoindoline, 1,1-trimethylenedioxy-3-imino-6-nitroisoindoline, 1,1-trimethylenedioxy-3-imino-7-nitroisoindoline, 1,1-trimethylenedioxy-3-imino-4-diethylaminoisoindoline, 1,1-trimethylenedioxy-3-imino-5-diethylaminoisoindoline, 1,1-trimethylenedioxy-3-imino-6-diethylaminoisoindoline, 1,1-trimethylenedioxy-3-imino-7-diethylaminoisoindoline, 1-isopropoxy-3-iminoisoindoline, 1-isobutoxy-3-iminoisoindoline, 1-t-butoxy-3-iminoisoindoline, 1-methoxy-3-imino-4,7-diaza-5,6-dimethylisoindoline, 1-ethoxy-3-imino-4,7-diaza-5,6-dimethylisoindoline, 1-n-propoxy-3-imino-4,7-diaza-5,6-dimethylisoindoline, 1-n-butoxy-3-imino-4,7-diaza-5,6-dimethylisoindoline, 1-methoxy-3-imino-4,7-diaza-5,6-diethylisoindoline, 1-ethoxy-3-imino-4,7-diaza-5,6-diethylisoindoline, 1-n-propoxy-3-imino-4,7-diaza-5,6-diethylisoindoline, 1-n-butoxy-3-imino-4,7-diaza-5,6-diethylisoindoline, 1-methoxy-3-imino-4,7-diaza-5,6-diphenylisoindoline, 1-ethoxy-3-imino-4,7-diaza-5,6-diphenylisoindoline, 1-n-propoxy-3-imino-4,7-diaza-5,6-diphenylisoindoline and 1-n-butoxy-3-imino-4,7-diaza-5,6-diphenylisoindoline.

The group $R^1$ in the carboxylic acid compound represented by the formula (5) which can be used in the present invention can be roughly classified into three groups of an aliphatic group, an aliphatic group including an aromatic group, and an aromatic group.

Examples of the substituent on the aliphatic group include halogen atoms such as fluorine, chlorine, bromine and iodine, a hydroxyl group, alkoxy groups having 1 to 4 carbon atoms, aryloxy groups, alkylthio groups having 1 to 4 carbon atoms, alkoxycarbonyl groups having 1 to 20 carbon atoms, an amino group and amido groups.

Examples of the aromatic group include a phenyl group, a naphthyl group and a biphenyl group.

Examples of the substituent on the aromatic group include halogen atoms such as fluorine, chlorine, bromine and iodine, a hydroxyl group, alkyl groups having 1 to 4 carbon atoms, alkoxy groups having 1 to 4 carbon atoms, alkylthio groups having 1 to 4 carbon atoms, a carboxyl group, an amino group, acyl groups and a nitro group.

When A is not =NH, typical examples of the compound represented by the formula (5) include aliphatic saturated carboxylic acids such as formic acid, acetic acid, propionic acid, butyric acid, isobutyric acid, valeric acid, trimethylacetic acid, caproic acid, enanthic acid, caprylic acid, nonanoic acid, decanoic acid, lauric acid, palmitic acid and stearic acid; aliphatic unsaturated carboxylic acids such as acrylic acid, vinylacetic acid and oleic acid; halogenated aliphatic carboxylic acids such as fluoroacetic acid, chloroacetic acid, bromoacetic acid, iodoacetic acid, dichloroacetic acid, trichloroacetic acid, α-chloropropionic acid and β-chloropropionic acid; aliphatic dicarboxylic acid monoesters such as monomethyl oxalate, monoethyl oxalate, monobutyl oxalate, monooctyl oxalate, monolauryl oxalate, monostearyl oxalate, monomethyl malonate, monoethyl malonate, monobutyl malonate, monooctyl malonate, monolauryl malonate, monostearyl malonate, monomethyl succinate, monoethyl succinate, monobutyl succinate, monooctyl succinate, monolauryl succinate, monostearyl succinate, monomethyl maleate, monoethyl maleate, monobutyl maleate, monooctyl maleate, monolauryl maleate and monostearyl maleate; aliphatic carboxylic acids having a hydroxyl group such as glycolic acid and lactic acid; aliphatic carboxylic acids having an alkoxy group such as methoxyacetic acid; aliphatic dicarboxylic acids such as oxalic acid, malonic acid, succinic acid, glutaric acid, maleic acid and fumaric acid; carboxylic acids having an aralkyl group such as phenylacetic acid, cinnamic acid, hydrocinnamic acid, γ-phenylbutyric acid, δ-phenylvaleric acid and ε-phenylcaproic acid; aromatic monocarboxylic acids such as benzoic acid, orthotoluic acid, metatoluic acid, paratoluic acid, paraethylbenzoic acid, parabutylbenzoic acid, orthochlorobenzoic acid, metachlorobenzoic acid, parachlorobenzoic acid, orthobromobenzoic acid, metabromobenzoic acid, parabromobenzoic acid, salicylic acid, metahydroxybenzoic acid, parahydroxybenzoic acid, paramethoxybenzoic acid, paraethoxybenzoic acid, anthranilic acid, metaaminobenzoic acid, paraaminobenzoic acid, metanitrolbenzoic acid and paraethylthiobenzoic acid; aromatic dicarboxylic acids such as phthalic acid, isophthalic acid, terephthalic acid, diphenic acid, naphthalene-1,4-dicarboxylic acid, naphthalene-1,5-dicarboxylic acid, naphthalene-1,8-dicarboxylic acid and naphthalene-2,6-dicarboxylic acid; aromatic polycarboxylic acids such as trimellitic acid and pyromellitic acid; and amino acids such as glycine, alanine, serine, cysteine, cysteine, aminobutyric acid, threonine, valine, methionine, leucine, isoleucine, phenylalanine, tyrosine, thyroxine, proline, hydroxypurine, tryptophan, aspartic acid, glutamic acid, arginine, lysine, ornithine and histidine.

In the case of a novel salt in which A is =NH in the formula (1), examples of the carboxylic acid represented by the formula (5) include benzoic acid, and benzoic acid derivatives such as chlorobenzoic acids, hydroxybenzoic acids, anisic acid, toluic acids and nitrobenzoic acids.

With regard to the color development sensitivity of the heat-sensitive recording material, the salts of the monobasic acids can exert a more excellent performance than the salts of the dibasic acids. Therefore, as the carboxylic acid which is used to form the carboxylate of the present invention, the monobasic acid is more preferable.

Typical examples of the carboxylates represented by the formulae (1) and (2) include salts formed by all the combinations of the above-mentioned imino compounds and carboxylic acids.

Next, reference will be made to a procedure of using the above-mentioned carboxylate compound as the heat-sensitive recording material.

The heat-sensitive recording material can be obtained by forming, on a support, a recording layer containing at least one of the above-mentioned carboxylate compounds capable of expressing a coloring state by heat. As the support, there can be used a paper, a synthetic paper, a synthetic resin film, a laminated paper or a non-woven sheet in compliance with a use purpose.

The recording layer can be fundamentally constituted of a color component and a binder, but the undermentioned additives can also be added.

As the color component, the carboxylate compound alone may be used, or at least one of the carbonyl compounds having a hydrogen atom at the α-position and/or at least one of the aromatic isocyanate compounds can be added as a coreactant.

The color component is dispersed in a binder solution by the use of an attritor or a sand mill. When two or more kinds of color components are used, they may be simultaneously mixed and dispersed, or they may be separately dispersed and then mixed to obtain a heat-sensitive coating solution. In this case, the color component may be in the state of suspended fine particles, or the color component may be dissolved and it may be in a solution state. The thus obtained heat-sensitive coating solution can be applied onto the support, followed by drying, to form the recording layer.

The weight ratio of the color component to the binder is preferably in the range of 1:1 to 1:0.01, more preferably 1:0.5 to 1:0.05.

Furthermore, the molar ratio of the carboxylate compound which is the color component to the carbonyl compound having the hydrogen atom at the α-position and/or the aromatic isocyanate compound is preferably in the range of 1:0.1 to 1:10, more preferably 1:0.4 to 1:4.

The carbonyl compound having a hydrogen atom at the α-position means a compound which has at least one carbonyl group and in which the hydrogen atom is bonded to the carbon atom (the α-position) adjacent to the carbonyl group, and typical examples of the carbonyl compound include compounds represented by the following formulae:

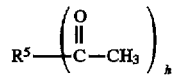

(wherein $R^5$ is an aliphatic compound residue having 1 to 12 carbon atoms or an aliphatic compound residue having an aromatic compound residue; and h is an integer of 1 to 6),

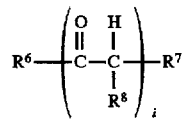

(wherein each of $R^6$ and $R^7$ is independently a hydrogen atom, an alkyl group having 1 to 4 carbon atoms, an aralkyl group or an aromatic compound residue, and $R^6$ and $R^7$ may bond to each other to form a ring; $R^8$ is a hydrogen atom, an alkyl group having 1 to 4 carbon atoms, an acyl group, an aralkyl group or an aromatic compound residue; and i is an integer of 1 to 6),

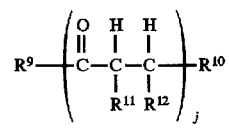

(wherein each of $R^9$, $R^{10}$, $R^{11}$ and $R^{12}$ is independently a hydrogen atom, an alkyl group having 1 to 4 carbon atoms, an acyl group, an aralkyl group or an aromatic compound residue, and $R^9$ and $R^{10}$ may bond to each other to form a ring; and j is an integer of 1 to 6),

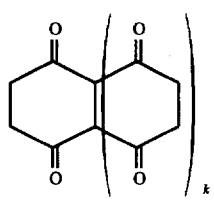

(k is an integer of 1 to 5),

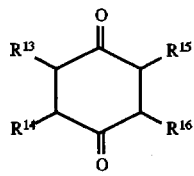

(wherein each of $R^{13}$, $R^{14}$, $R^{15}$ and $R^{16}$ is independently a hydrogen atom, a halogen atom, an alkyl group having 1 to 4 carbon atoms, an aralkyl group, a cyano group, an aromatic compound residue, or —$CO_2R^{17}$ ($R^{17}$ is a hydrogen atom, an alkyl group having 1 to 12 carbon atoms, an aralkyl group or an aromatic compound residue)).

Here, the residue means a monovalent group or a polyvalent group having a valence of two or more.

Examples of the aromatic compound residue include hydrocarbonaceous aromatic compounds such as a benzene ring, a naphthalene ring, a biphenyl ring, an anthracene ring, an indene ring, a fluorene ring, a phenanthrene ring and an acenaphthene ring; heterocyclic aromatic compounds such as a furan ring, a pyrrole ring, a thiophene ring, a benzofuran ring, an indole ring, an indazole ring, a coumarone ring, a benzimidazolone ring, a benzothiophene ring, a benzoxazole ring, a benzothiazole ring, a benzimidazole ring, a pyridine ring, a quinoline ring, an isoquinoline ring, a quinazoline ring, an acridine ring, a phenazine ring, a pyrazine ring, an oxazine ring, a xanthene ring, a purine ring, a dibenzofuran ring and a dibenzopyrrole ring; and their derivatives.

Usable examples of the halogen atoms include fluorine, chlorine, bromine and iondine, and fluorine and chlorine are preferable.

Suitable usable examples of the acyl group include aliphatic acyl groups such as an acetyl group, a propionyl group and a butyroyl group; and aromatic acyl groups such as a benzoyl group and a nicotinoyl group.

In the preferable aralkyl group, its alkyl moiety preferably has 1 to 4 carbon atoms, and its aryl moiety preferably is a benzene ring, a naphthalene ring, a biphenyl ring or an indene ring.

Typical examples of the carbonyl compound having a hydrogen atom at the α-position include monoketones such as acetophenone; diketones such as 1-phenyl-1,2-propanedione, acetylacetone, 3,4-hexanedione, 2,5-hexanedione, 1-phenyl-1,3-butanedione, 2,3-dicyano-1,4-cyclohexanedione, dibenzoylmethane, 2,4-pentanedione, 1,3-cyclopentanedione, 1,3-hexanedione, 1,2-cyclohexanedione, 1,3-cyclohexanedione, 1,4-cyclohexanedione, 1,2-diacetylbenzene, 1,4-cyclohexanedione-2,5-dicarboxylic acid, diethyl-1,4-cyclohexanedione-2,5-dicarboxylate, dibutyl-1,4-cyclohexanedione-2,5-dicarboxylate and dioctyl-1,4-cyclohexanedione-2,5-dicarboxylate; triketones such as triacetylmethane, 1,1,2-triacetylethane, 1,2,3-triacetylpropane, 2,4,6-heptanetrione and 1,3,5-cyclohexanetrione; and tetraketones such as 1,1,2,2-tetraacetylethane and 1,4,5,8-decalintetraone. They may be used singly or in a combination of two or more thereof.

The aromatic isocyanate which can be used in the present invention is a colorless or a lightly colored compound which is solid at ordinary temperature, and typical examples of this aromatic isocyanate include 4-chlorophenyl isocyanate, 2,6-dichlorophenyl isocyanate, 1,2-phenylene diisocyanate, 1,3-phenylene diisocyanate, 1,4-phenylene diisocyanate, 1-methylbenzene-2,4-diisocyanate, 1-methoxybenzene-2,4-diisocyanate, 1-ethoxybenzene-2,4-diisocyanate, 1-chlorobenzene-2,5-diisocyanate, 1,3-dimethylbenzene-4,6-diisocyanate, 1,4-dimethylbenzene-2,5-diisocyanate, 1-methoxybenzene-2,5-diisocyanate, 2,5-dimethoxybenzene-1,4-diisocyanate, 2,5-diethoxybenzene-1,4-diisocyanate, 2,5-dibutoxybenzene-1,4-diisocyanate, azobenzene-4,4'-diisocyanate, diphenyl ether 4,4'-diisocyanate, naphthalene-1,4-diisocyanate, naphthalene-1,5-diisocyanate, naphthalene-2,6-diisocyanate, naphthalene-2,7-diisocyanate, 3,3'-dimethylbiphenyl-4,4'-diisocyanate, 3,3'-dimethoxybiphenyl-4,4'-diisocyanate, 3,3'-dichloro-4,4'-diphenyl-diisocyanate, 3,3'-dimethyl-4,4'-diphenyl-diisocyanate, 4,4'-diphenylmethane-diisocyanate, 4,4'-benzophenone-diisocyanate, diphenylsulfone-4,4'-diisocyanate, 4,4'-benzanilide-diisocyanate, benzophenone-3,3'-diisocyanate, fluorene-2,7-diisocyanate, anthraquinone-2,6-diisocyanate, 9-ethylcarbazole-3,6-diisocyanate, pyrene-3,8-diisocyanate, naphthalene-1,3,7-triisocyanate, biphenyl-2,4,4'-triisocyanate, 4,4',4"-triisocyanato-2,5-dimethoxytriphenylamine, 4-dimethylaminophenyl isocyanate and tris(4-phenylisocyanato) thiophosphate.

They can be used singly or in a combination of two or more thereof. Furthermore, they can each be used as a block isocyanate which is an addition compound with a phenol, a lactam or an oxime, if necessary, and they can also each be used as an isocyanurate which is a dimer or a trimer of the diisocyanate. Moreover, they can also each be used as a polyisocyanate obtained by the addition of a polyol.

To this recording layer, various kinds of additives can be added in compliance with the intended purpose, and examples of the additives include a melting point depressant, an ultraviolet light absorber, an antioxidant, and organic and inorganic pigments.

Examples of the melting point depressant include waxes such as paraffin wax, polyethylene wax, higher fatty acids and their esters; acid amides such as amide stearate; diphenyls such as 4,4'-dimethylbiphenyl; methylolamides; naphthalenes such as 1,3-dinitronaphthalene; ureas; acids such as phthalic anhydride; anilides such as acetoanilide, benzanilide and anilide alkylcarboxylates; triphenyls; phthalonitriles; ethers such as bisresorcinol ethylene ether; salicylic acid derivatives such as 4-t-butyl salicylate; ethyl 2-cyano-3,3-diphenylacrylate; benzotriazoles; fluorene; dimethyl isophthalate; diphenyl sulfone; mandelic acid; benzoin; ethylanthraquinone; coumarone compounds; carbazoles such as N-ethylcarbazole; sulfonamides; triphenylmethanes; thiazoles such as dibenzothiazyl disulfide; sulfenamides such as N-cyclohexyl-2-benzothiazolylsulfenamide; thiurams such as tetramethylthiuram disulfide; dithioates such as zinc dibutyldithiocarbamate; guanidines such as diphenylguanidine; thioureas such as N,N-diphenylthiourea; phenylhydrazide derivatives of carboxylic acid; p-hydroxybenzoates; and amides such as N,N-diphenylformamide.

Examples of the ultraviolet light absorber include benzotriazole and its derivatives, benzoin and its derivatives, 2-chloroanthraquinone, benzoyl peroxide, salicylates such as p-t-butylphenyl salicylate and cyanoacrylates such as ethyl diphenylacrylate.

Examples of the antioxidant include 2,6-di-t-butyl-4-methylphenol, di(3-t-butyl-4-hydroxy-5-methylphenyl) thioether, hindered phenols such as 1,1-bis(2-methyl-4-hydroxy-5-t-butylphenyl)butane, and hindered amines such as di(2,2,6,6-tetramethyl-4-piperidine) sebacate.

Examples of the pigment include talc, clay, silica, calcined kaolin, zinc oxide, silicon oxide, titanium oxide, aluminum hydroxide, calcium carbonate, magnesium carbonate, and urea-formaldehyde resins.

Examples of a dispersion medium for a binder solution include water and organic solvents such as toluene, methanol, ethanol, isopropyl alcohol, n-hexane, cyclohexane, n-octanol, ethylcyclohexane and dioxane.

Usable examples of the binder in the case that the dispersion medium is water include polyvinyl alcohol resins, methyl cellulose resins, hydroxyethyl celluose resins, carboxymethyl cellulose resins, methyl vinyl ether/maleic anhydride copolymer resins, polyacrylic acid resins, polyvinyl pyrrolidone resins, acrylamide resins, gelatin and gum arabic.

Examples of the binder in the case that the dispersion medium is the organic solvent include alkyd resins, vinyl chloride resins, urethane resins, xylene resins, phenolic resins, coumarone resins, vinyltoluene resins, terpene resins, vinyltoluene/butadiene copolymer resins, vinyltoluene/acrylate copolymer resins, styrene/acrylate copolymer resins and vinyl/isobutyl ether copolymer resins.

Furthermore, on the recording layer, a protective layer can be formed, and under the recording layer, an undercoat can be formed.

For the protective layer, there can be used urethane resins, polyolefin resins, polyester resins, vinyl resins, epoxy resins and acrylic resins.

For the undercoat which can improve coloring properties, there can be used insulating fine hollow particles, calcined kaolin, organic pigments and thermally expanded microcapsules.

In the case that the heat-sensitive recording material of the present invention is used as a heat-sensitive recording label, the heat-sensitive recording layer is formed on the support, and if necessary, an overcoat can be formed thereon, but each layer is subjected to a supercalender treatment after the formation of each layer. Next, an adhesive layer and a release sheet is attached to the back surface of the support (the surface opposite to the surface having the heat-sensitive recording layer of the support), thereby obtaining the heat-sensitive recording label.

In general, as a method for forming an adhesive label, there is used a method which comprises applying an adhesive on the release layer of a release sheet, drying it to form an adhesive layer, and then sticking a heat-sensitive recording member (which comprises a support and a heat-sensitive recording layer formed on the support) on the adhesive layer.

Examples of the adhesive include rubber emulsions, acrylic emulsions, vinyl ether emulsions, solvent-containing adhesives and solvent-free adhesives.

Examples of the release sheet include high-density base papers such as glassine paper, clay-coated paper, kraft paper, and polylaminate paper coated with a fluoroplastic or a silicone resin.

The amount of the overcoat layer is preferably in the range of 3 to 12 g/m$^2$ in terms of a dry layer, the amount of the heat-sensitive recording layer is preferably in the range of 2 to 10 g/m$^2$ in terms of a dry layer, and the amount of the adhesive layer is preferably in the range of 5 to 50 g/m$^2$ in terms of a dry layer.

In the case that the heat-sensitive recording material of the present invention is used as an information recording card, as the support, there can be selected a fine paper or a plastic film having stiffness necessary for the portable card and a thickness of 10 to 500 μm, and examples of the plastics include polyesters such as polyethylene terephthalate and polybutylene terephthalate, acrylic resins such as polymethyl methacrylate, polymethyl acrylate and polyethyl methacrylate, polystyrene, acrylonitrile/butadiene/styrene copolymer, cellulose triacetate, polyvinyl chloride and polycarbonates. On the selected support, the heat-sensitive recording layer can be formed to obtain the desired information recording card.

A recorded image on the information recording card of the present invention is resistant to water, oils, plasticizers, chemicals and light, and so the overcoat layer is not always necessary. However, for the purpose of preventing an uncolored portion from soiling, the overcoat layer may be formed.

As the material for the overcoat layer, there can be used urethane resins, polyolefin resins, polyester resins, vinyl resins, epoxy resins and acrylic resins, and to this overcoat layer, the above-mentioned organic and inorganic pigments as well as a lubricant can be added. Examples of the lubricant include zinc stearate, calcium stearate, polyethylene waxes, carnauba waxes, paraffin waxes and ester waxes.

In the information recording card of the present invention, not only visual information but also code information can be recorded by utilizing reversible recording such as optical recording, thermal recording (cloudy recording, or the use of a leuco-dye or the like), electric recording (an IC card), optical magnetic recording or thermal magnetic recording in addition to the irreversible heat-sensitive recording which has been described above.

A magnetic recording layer can be formed between the support and the irreversible heat-sensitive recording layer, or on a surface opposite to the surface having the irreversible heat-sensitive recording layer of the support.

The magnetic recording layer can be formed by mixing a magnetic powder, carbon black, a dispersant and a binder in an organic solvent, applying the mixture on the support, subjecting the mixture film to magnetic field orientation in a horizontal magnetic field, and then drying it. The thickness of the magnetic recording layer is preferably in the range of 10 to 15 μm.

On the magnetic recording layer, a protective layer or a concealing layer can be formed. As materials for the protective layer and the concealing layer, there can be used the above-mentioned materials for the overcoat layer. The concealing layer can be obtained by adding a pigment to the above-mentioned materials, and then dispersing the same therein.

The cloudy recording layer is usually formed on a surface opposite to the surface having the irreversible heat-sensitive recording layer of the support, but both the layers can be formed on the same side of the support, so long as they are not directly superposed upon each other.

The cloudy recording layer mainly comprises a resin matrix and an organic low-molecular weight substance dispersed in this resin matrix. This recording layer utilizes a polycrystalline organic low-molecular weight substance which scatters incident light at low temperature, whereby the layer becomes a cloudy opaque state, and when heat is applied, the organic low-molecular weight substance becomes a single crystalline state from the polycrystalline state via a semi-melting state, whereby the incident light can pass through the layer without being scattered and so the recording layer becomes transparent.

The cloudy recording layer can be formed by dissolving the resin matrix in a solvent, dispersing the organic low-molecular weight substance in the solution so that the substance may be in the state of fine particles, applying the resultant dispersion onto the surface of the support or a surface on which the cloudy recording layer should be formed, and then drying the dispersion.

Examples of a usable material for the resin matrix include chlorinated vinyl chloride resins, phenoxy resins, styrol resins, polymethyl methacrylates, polyesters, polyamides, polystyrenes, polydivinylbenzenes, polycarbonates, polyvinylformals and their polymers.

Examples of the usable organic low-molecular weight substance include higher alcohols, aliphatic saturated carboxylic acids, derivatives of these carboxylic acids, and higher ketones.

Typical examples of the organic low-molecular weight substance include higher alcohols such as pentadecanol, heptadecanol, octadecanol, eicosanol, docosanol, tetracosanol, hexacosanol, octacosanol and triacontanol; higher saturated carboxylic acids such as capric acid, lauric acid, myristic acid, palmitic acid, stearic acid, nonadecanoic acid, arachic acid, heneicosanic acid, behenic acid, tricosanoic acid, lignoceric acid, pentacosanoic acid, cerotic acid, heptacosanoic acid, montanic acid, nonacosanoic acid, melissic acid, hentriacontanoic acid, lacceric acid, tritriacontanoic acid, geddic acid, ceroplastic acid, hexatriacontanoic acid, heptatriacontanoic acid, nonatriacontanoic acid and tetracontanoic acid; aliphatic saturated dicarboxylic acids such as dodecanoic diacid, tridecanoic diacid, tetradecanoic diacid, pentadecanoic diacid, hexadecanoic diacid, octadecanoic diacid, nonadecanoic diacid, eicosanic diacid, heneicosanic diacid, docosanoic diacid, tricosanoic diacid, tetracosanoic diacid, hexacosanoic diacid, triacontanoic diacid and tetratriacontanoic diacid; and higher ketones such as 8-pentadecanone, 9-heptadecanone, 10-nonadecanone, 11-heneicosanone, 12-tricosanone, 14-heptacosanone, 16-hentriacontanone, 18-pentatriacontanone, 22-tritetracontanone, 2-pentadecanone, 2-heptadecanone, 2-octadecanone, 2-nonadecanone, cyclopentadecanone, cyclohexadecanone, cyclooctadecanone, cyclononadecanone, cycloeicosanone, cyclodocosanone, cyclotricosanone, cyclopentacosanone, cyclohexagosanone and cyclononacosanone.

The solvent to be used can be selected in compliance with the kinds of resin matrix and organic low-molecular weight substance, and examples of the solvent include tetrahydrofuran, methyl ethyl ketone, methyl isobutyl ketone, chloroform, carbon tetrachloride, ethanol, toluene and benzene.

To the cloudy recording layer, an additive such as a surface active agent or a high boiling point solvent can be added besides the above-mentioned components, for the purpose of making the formation of the transparent image easy.

Examples of the surface active agent include esters of polyvalent alcohols and higher fatty acids, higher alkyl ethers of polyvalent alcholls, higher alcohols, higher alkylphenols, higher alkylamines of higher fatty acids, higher fatty acid amides, sodium higher alkylbenzenesulfonate, calcium higher alkylbenzenesulfonate, barium higher alkylbenzenesulfonate and magnesium higher alkylbenzenesulfonate.

Examples of the high boiling point solvent include tributyl phosphate, tri(2-ethylhexyl) phosphate, triphenyl phosphate, tricresyl phosphate, butyl oleate, dimethyl phthalate, diethyl phthalate, dibutyl phthalate, diheptyl phthalate, di(n-octyl) phthalate, di(n-ethylhexyl) phthalate, diisononyl phthalate, dioctyldecyl phthalate, diisodecyl phthalate, butylbenzyl phthalate, dibutyl adipate, di(n-hexyl) adipate, di(2-ethylhexyl) adipate, di(2-ethylhexyl) azelate, dibutyl sebacate, di(2-ethylhexyl) sebacate, diethylene glycol dibenzoate, triethylene glycol 2-ethylbutyrate, methyl acetylricinoleate, butyl acetylricinoleate, butylphthalylbutyl glycolate and tributyl acetylcitrate.

The reversible heat-sensitive recording layer comprises three components of a leuco-pigment, a developer and a binder, and on the reversible heat-sensitive recording layer, recording is possible with less heat than on the irreversible heat-sensitive recording layer. If transmission properties are imparted to the reversible heat-sensitive recording layer, it can be formed on the irreversible heat-sensitive recording layer.

The formation of the reversible heat-sensitive recording layer on the support can usually be carried out by employing a method which comprises uniformly dispersing or dissolving the leuco-pigment, the developer and the binder in water or the organic solvent, adding, if necessary, improvers such as a sensitizer and a white pigment, applying the resultant coating solution onto the support by the use of a bar, a blade or an air-knife, and then drying it.

The thickness of the reversible heat-sensitive recording layer is preferably in the range of 2 to 20 μm.

Typical examples of the leuco-pigment include crystal violet lactone, 2-(2-chloroanilino)-6-diethylaminofluoran, 2-anilino-3-methyl-6-dibutylaminofluoran, 2-(2-chloroanilino)-6-dibutylaminofluoran, 2-(3-trifluoromethylanilino)-6-diethylaminofluoran, 2-(3-trifluoromethylanilino)-6-dibutylaminofluoran, 2-anilino-3-methyl-6-(N-ethyl-N-isoamylamino)fluoran, 2-anilino-3-methyl-6-diethylaminofluoran, 2-anilino-3-methyl-6-(N-ethyl-N-4-toluylamino)-fluoran, 2-anilino-3-methyl-6-pyrrolidinofluoran and 2-anilino-3-methyl-6-piperidinofluoran.

As the developer, an amine salt of a carboxylic acid can be used.

Typical examples of the carboxylic acid include gallic acid, 2-hydroxybenzoic acid, 3-hydroxybenzoic acid, 4-hydroxybenzoic acid, 3,4-dihydroxybenzoic acid, 3,5-dihydroxybenzoic acid, 2,3-dihydroxybenzoic acid, 2,4-dihydroxybenzoinc acid, 2,5-dihydroxybenzoic acid, 2,6-dihydroxybenzoic acid, 3,6-dihydroxybenzoic acid, 4,5-dihydroxybenzoic acid, 4,6-dihydroxybenzoic acid, gentisic acid, protocatechuic acid, 2,3,4-trihydroxybenozoic acid, 2,4,6-trihydroxybenozoic acid, hydroxy-o-toluic acid, hydroxy-m-toluic acid, hydroxy-p-toluic acid, hydroxyphthalic acid, hydroxyisophthalic acid, 5-methoxysalicylic acid, caffeic acid, umbellic acid, hydroxyphenylacetic acid, 3-(hydroxyphenyl)propionic acid and hydroferulic acid.

Examples of the amine include aliphatic amines such as n-hexylamine, n-heptylamine, n-octylamine, 2-ethylhexylamine, n-nonylamine, n-decylamine, n-undecylamine, n-dodecylamine, n-tetradecylamine, n-hexadecylamine n-octadecylamine; alicyclic amines such as cyclohexylamine, 4-methylcyclohexylamine, dicyclohexylamine, cyclooctylamine, cyclododecylamine and adamantaneamine; aralkylamines such as benzylamine, dibenzylamine, 1,2-diphenylethylamine, 2,2-diphenylethylamine, 3,3-diphenylethylamine, 2-phenylethylamine, 3-phenylpropylamine, 4-phenylbutylamine and triphenylmethylamine; and aromatic amines such as aniline, toluidine, aminodiphenyl, anisidine, diaminotoluene, xylidine, benzidine and tolidine.

Typical examples of the binder for the reversible heat-sensitive recording layer include polyvinyl alcohol, ethyl cellulose, cellulose acetate, polystyrene, polyvinyl chloride, acrylic resin, polyurethane, polyvinyl butyral and nitrocellulose.

Next, the present invention will be described in more detail with reference to examples. However, the scope of the present invention should not be limited to these examples.

In these examples, % and part(s) mean % by weight and part(s) by weight.

In Examples 1 to 41 and Reference Examples 1 to 20, the synthesis of carbonates will be described. Diiminoisoindoline derivatives [compounds represented by the formula (3) in which A is =NH] which were used as materials were obtained from anhydrides, imides, amides, dinitriles or the like of corresponding dicarboxylic acids in known manners (Japanese Patent Application Laid-open No. 280083/1988 and the like). The compounds represented by the formula (3) in which A is a group other than =NH and the compounds represented by the formula (4) were obtained from phthalonitriles by referring to Angewandte Chemie, 68, p. 134 (1956).

EXAMPLE 1

(1,3-diiminoisoindoline benzoate)

To 10 ml of methanol was added 1.45 g of 1,3-diiminoisoindoline, and the solution was then stirred under reflux to dissolve the 1,3-diiminoisoindoline. Afterward, 1.22 g of benzoic acid was added to this methanol solution, and stirring was further continued for 5 minutes under reflux. After cooling, the resultant precipitate was collected by filtration, and then washed with 5 ml of methanol. After drying, 2.54 g (yield=95%) of a white powder was obtained. The melting point and the values of elemental analysis of the obtained compound were as follows. The infrared absorption spectrum of the compound is shown in FIG. 1.

Melting point: 184° to 186° C. (decomposition occurred)
Values of elemental analysis:

|  | C (%) | H (%) | N (%) |
|---|---|---|---|
| Calcd. ($C_{15}H_{13}N_3O_2$) | 67.40 | 4.90 | 15.72 |
| Found | 67.21 | 4.92 | 15.59 |

EXAMPLES 2 to 16

The same procedure as in Example 1 was carried out to obtain carboxylates of Examples 2 to 16. The results of these examples are all shown in Table 1.

TABLE 1

| | Obtained carboxylate (1) | Yield (%) | Powder color | Melting point |
|---|---|---|---|---|
| Example 2 | 1,3-Diiminoisoindoline orthotoluylate | 98 | White | 158–159° C. (Dec.) |
| Example 3 | 1,3-Diiminoisoindoline orthochlorobenzoate | 95 | White | 175–176° C. (Dec.) |
| Example 4 | 1,3-Diiminoisoindoline methachlorobenzoate | 92 | White | 156–157° C. (Dec.) |
| Example 5 | 1,3-Diiminoisoindoline parachlorobenzoate | 98 | White | 191–193° C. (Dec.) |
| Example 6 | 1,3-Diiminoisoindoline salicylate | 94 | White | 185–186° C. (Dec.) |
| Example 7 | 1,3-Diiminoisoindoline paraaminobenzoate | 86 | Yellow | 285–286° C. (Dec.) |
| Example 8 | 1,3-Diiminoisoindoline 2-benzoylbenzoate | 94 | White | 210–212° C. (Dec.) |
| Example 9 | 1,3-Diiminoisoindoline p-anisate | 94 | White | 163–165° C. (Dec.) |
| Example 10 | 1,3-Diimino-4-(2,4-di- | 75 | White | 144–145° C. |

TABLE 1-continued

| | Obtained carboxylate (1) | Yield (%) | Powder color | Melting point |
|---|---|---|---|---|
| | methylpentoxy)-isoindoline paratoluylate | | | (Dec.) |
| Example 11 | 1,3-Diimino-4-ethoxy-isoindoline paratoluylate | 97 | White | 200–202° C. (Dec.) |
| Example 12 | 1,3-Diimino-4-n-hepthyloxy isoindoline paratoluylate | 99 | White | 188–190° C. (Dec.) |
| Example 13 | 1,3-Diimino-4-nitro-isoindoline paraanisate | 84 | Pale yellow | 159–162° C. (Dec.) |
| Example 14 | 1,3-Diimino-4,7-dihydroxy-isoindoline parachlorobenzoate | 33 | Yellow | 253–258° C. (Dec.) |
| Example 15 | 1,3-Diimino-5-n-heptyl-isoindoline parachlorobenzoate | 82 | Pale yellow | 166–168° C. (Dec.) |
| Example 16 | 1,3-Diimino-4,7-diaza-5,6-dimethylisoindoline benzoate | 69 | Pale yellow | 120–121° C. (Dec.0 |

REFERENCE EXAMPLES 1 to 20

The same procedure as in Example 1 was carried out to obtain carboxylates of Reference Examples 1 to 20. The results of these reference examples are all shown in Table 2.

TABLE 2

| | Obtained carboxylate (1) | Yield (%) | Powder color | Melting point |
|---|---|---|---|---|
| Reference Example 1 | 1,3-Diiminoisoindoline butyrate | 96 | White | 112–116° C. (Dec.) |
| Reference Example 2 | 1,3-Diiminoisoindoline acetate | 96 | White | 155–157° C. (Dec.) |
| Reference Example 3 | 1,3-Diiminoisoindoline lactate | 99 | White | 179–181° C. (Dec.) |
| Reference Example 4 | 1,3-Diiminoisoindoline phenoxyacetate | 94 | White | 210–212° C. (Dec.) |
| Reference Example 5 | 1,3-Diiminoisoindoline isophthalate | 82 | White | ≧300° C. |
| Reference Example 6 | 1,3-Diiminoisoindoline monochloroacetate | 99 | White | 228–230° C. (Dec.) |
| Reference Example 7 | 1,3-Diiminoisoindoline oleate | 91 | White | 124–129° C. (Dec.) |
| Reference Example 8 | 1,3-Diiminoisoindoline trimethylacetate | 84 | White | 250–252° C. (Dec.) |
| Reference Example 9 | 1,3-Diiminoisoindoline L-phenylalanine salt | 99 | White | 155–157° C. (Dec.) |
| Reference Example 10 | 1,3-Diiminoisoindoline methoxyacetate | 100 | White | 171–173° C. (Dec.) |
| Reference Example 11 | 1,3-Diiminoisoindoline laurate | 94 | White | 135–137° C. (Dec.) |
| Reference Example 12 | 1,3-Diiminoisoindoline succinic acid monoethyl ester salt | 98 | White | 181–183° C. (Dec.) |
| Reference Example 13 | 1,3-Diiminoisoindoline succinic acid monooctyl ester salt | 93 | White | 128–130° C. (Dec.) |
| Reference Example 14 | 1,3-Diiminoisoindoline succinic acid monostearyl ester salt | 94 | White | 135–137° C. (Dec.) |
| Reference Example 15 | 1,3-Diimino-5-t-butyl-isoindoline acetate | 100 | White | 136–138° C. (Dec.) |
| Reference Example 16 | 1,3-Diimino-5-t-amyl-isoindoline acetate | 90 | White | 173–175° C. (Dec.) |
| Reference Example 17 | 1,3-Diimino-5-t-amylbenz-isoindoline acetate | 90 | White | 202–204° C. (Dec.) |
| Reference Example 18 | 1,3-Diimino-6-chlorobenz-isoindoline methoxyacetate | 100 | White | ≧310° C. |
| Reference Example 19 | 1,3-Diimino-6-bromobenz-isoindoline methoxyacetate | 81 | White | 263–265° C. (Dec.) |
| Reference Example | 1,3-Diimino-4,5,6,7-tetra- | 92 | Orange | 181–183° C. |

TABLE 2-continued

| | Obtained carboxylate (1) | Yield (%) | Powder color | Melting point |
|---|---|---|---|---|
| Example 20 | phenylthioisoindoline acetate | | | (Dec.) |

EXAMPLE 17

( 1,1-dimethoxy-3-iminoisoindoline p-tolugiate)

Figure 2:
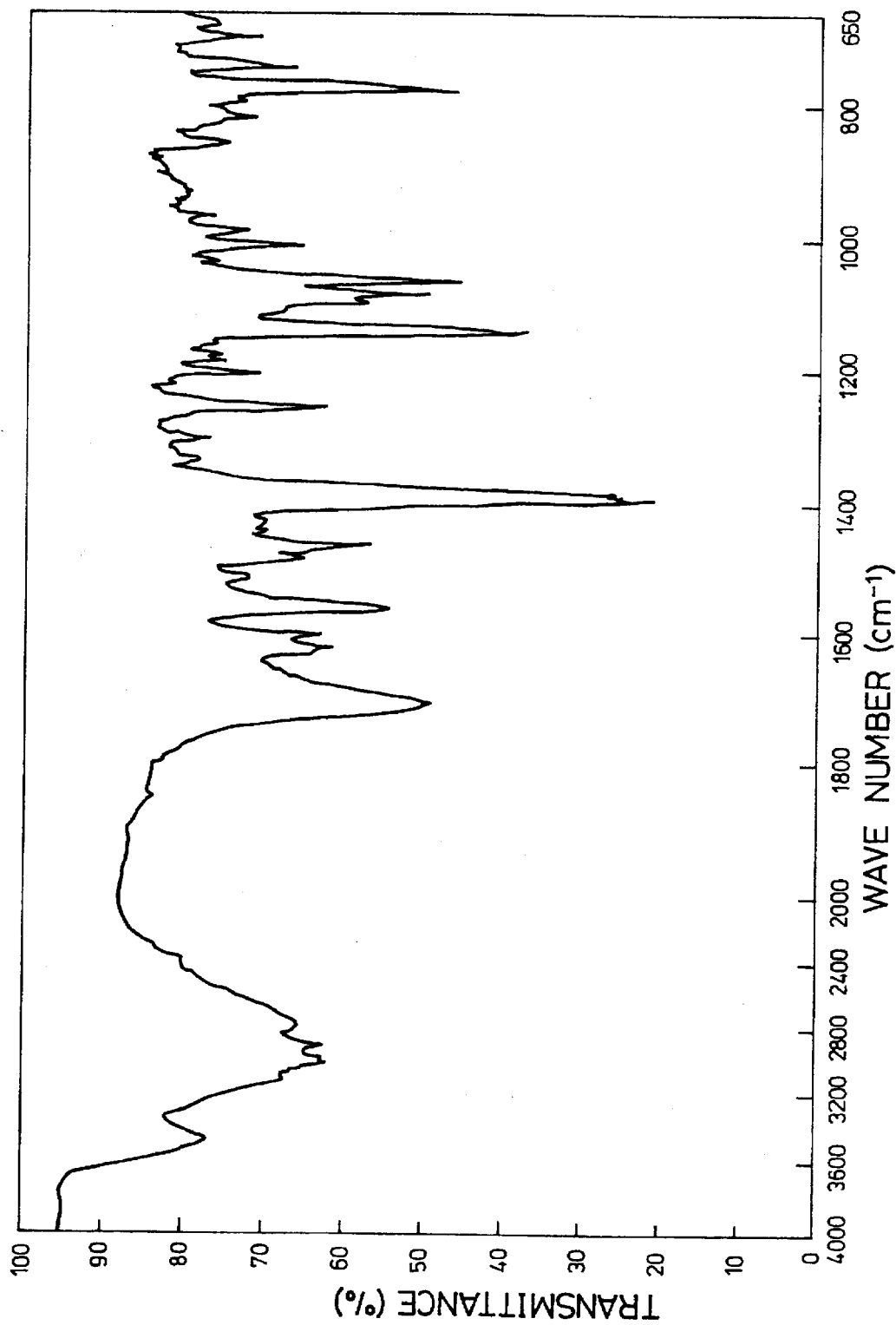
FIG. 2 shows the infrared absorption spectrum of a compound obtained in Example 17.

To a mixture of 1.92 g (0.01 mol) of 1,1-dimethoxy-3-iminoisoindoline and 1.36 g (0.01 mol) of p-toluic acid was added 10 ml of acetone at 15° to 20° C., followed by stirring for 30 minutes. After once the solution became transparent, the resultant white precipitate was collected by filtration, and then washed with 5 ml of acetone. After drying, 3.21 g (yield=98%) of a white powder was obtained. The melting point and the values of elemental analysis of the obtained compound were as follows. The infrared absorption spectrum of the compound is shown in FIG. 2.

Melting point: 98° to 99° C. (decomposition occurred)

| | Values of elemental analysis: | | |
|---|---|---|---|
| | C (%) | H (%) | N (%) |
| Calcd. ($C_{18}H_{20}N_2O_4$) | 65.64 | 6.14 | 8.53 |
| Found | 65.92 | 6.10 | 8.49 |

EXAMPLES 18 to 41

The same procedure as in Example 17 was carried out to obtain carboxylates of Examples 18 to 41. The results of these examples are all shown in Table 3.

TABLE 3

| | Obtained carboxylate (1) | Yield (%) | Powder color | Melting point |
|---|---|---|---|---|
| Example 18 | 1,1-Dimethoxy-3-iminoiso-indoline orthotoluylate | 95 | White | 82–83° C. (Dec.) |
| Example 19 | 1,1-Dimethoxy-3-iminoiso-indoline parachlorobenzoate | 88 | White | 144–145° C. (Dec.) |
| Example 20 | 1,1-Dimethoxy-3-iminoiso-indoline paraanisate | 99 | White | 160–161° C. (Dec.) |
| Example 21 | 1,1-Dimethoxy-3-iminoiso-indoline paranitrobenzoate | 100 | Slightly yellowish white | 136–138° C. (Dec.) |
| Example 22 | 1,1-Dimethoxy-3-iminoiso-indoline methoxyacetate | 98 | White | 84–85° C. (Dec.) |
| Example 23 | 1,1-Dimethoxy-3-iminoiso-indoline laurate | 69 | White | 63–64° C. |
| Example 24 | 1,1-Dimethoxy-3-iminoiso-indoline succinic acid monomethyl ester salt | 94 | White | 81.5–82.5° C. |
| Example 25 | 1,1-Dimethoxy-3-iminoiso-indoline succinic acid monobenzyl ester salt | 93 | White | 77–82° C. |
| Example 26 | 1,1-Dimethoxy-3-iminoiso-indoline succinic acid monostearyl ester salt | 100 | Slightly yellowish white | 63–65° C. |
| Example 27 | 1,1-Ethylenedioxy-3-imino-isoindoline orthotoluylate | 99 | White | 152–153° C. (Dec.) |
| Example 28 | 1,1-Diethoxy-3-iminoiso-indoline paratoluylate | 96 | White | 75–76° C. (Dec.) |
| Example 29 | 1-Iso-propoxy-1-methoxy-3-iminoisoindoline para-nitrobenzoate | 99 | Slightly yellowish white | 125–127° C. (Dec.) |
| Example 30 | 1,1-(1'-Methylethylene-dioxy)-3-iminoisoindoline paratoluylate | 98 | White | 173–174° C. (Dec.) |
| Example 31 | 1,1-(1'-Ethylethylene-dioxy)-3-iminoisoindoline parachlorobenzoate | 96 | White | 132–133° C. |
| Example 32 | 1,1-(1'-n-Propylethylene-dioxy)-3-iminoisoindoline parachlorobenzoate | 94 | White | 131–132° C. |
| Example 33 | 1,1-(1'-n-Butylethylene-dioxy)-3-iminoisoindoline parachlorobenzoate | 93 | White | 160–161° C. |
| Example 34 | 1,1-(1'-Methoxymethyl-ethylenedioxy)-3-iminoiso-indoline parachlorobenzoate | 94 | White | 131–132° C. |
| Example 35 | 1,1-(1'-Allyloxymethyl-ethylenedioxy)-3-iminoiso-indoline parachlorobenzoate | 92 | White | 135–137° C. |
| Example 36 | 1,1-(1'-Methyltrimethylene-dioxy)-3-iminoisoindoline parachlorobenzoate | 98 | White | 146–147° C. (Dec.) |
| Example 37 | 1,1-(1',1',3'-Trimethyl-trimethylenedioxy)-3-iminoisoindoline paratoluylate | 98 | White | 158–159° C. (Dec.) |
| Example 38 | 1-Isopropoxy-3-iminoiso-indoline parachlorobenzoate | 93 | White | 126–127° C. (Dec.) |
| Example 39 | 1-Methoxy-3-imino-4,7-diaza-5,6-diethyliso-indolenine parachloro-benzoate | 85 | White | 190–194° C. (Dec.) |
| Example 40 | 1-Methoxy-3-imino-4,7-diaza-5,6-diphenyliso indolenine methatoluylate | 100 | White | 162.5–163.5° C. (Dec.) |
| Example 41 | 1,1-Dimethoxy-3-imino-4-n-butoxyisoindoline paratoluylate | 96 | White | 95–96° C. (Dec.) |

EXAMPLE 42

(Preparation of heat-sensitive recording material)

To 10 parts of a 5% aqueous polyvinyl alcohol solution was added 1 part of 1,3-diiminoisoindoline benzoate obtained in Example 1, and the solution was then milled by a sand mill so that an average particle diameter of the benzoate might be 1.5 μm or less, to obtain a dispersion.

Next, 4 parts of a 60% aqueous light-duty calcium carbonate dispersion was added to the above-mentioned dispersion, and they were then sufficiently mixed to obtain a heat-sensitive coating solution.

This heat-sensitive coating solution was applied onto a fine paper by the use of a Meyer bar No. 10 so that the amount of the coating solution might be 6 g/m² in terms of a solid content, and then dried to obtain a heat-sensitive recording material.

Figure 3:
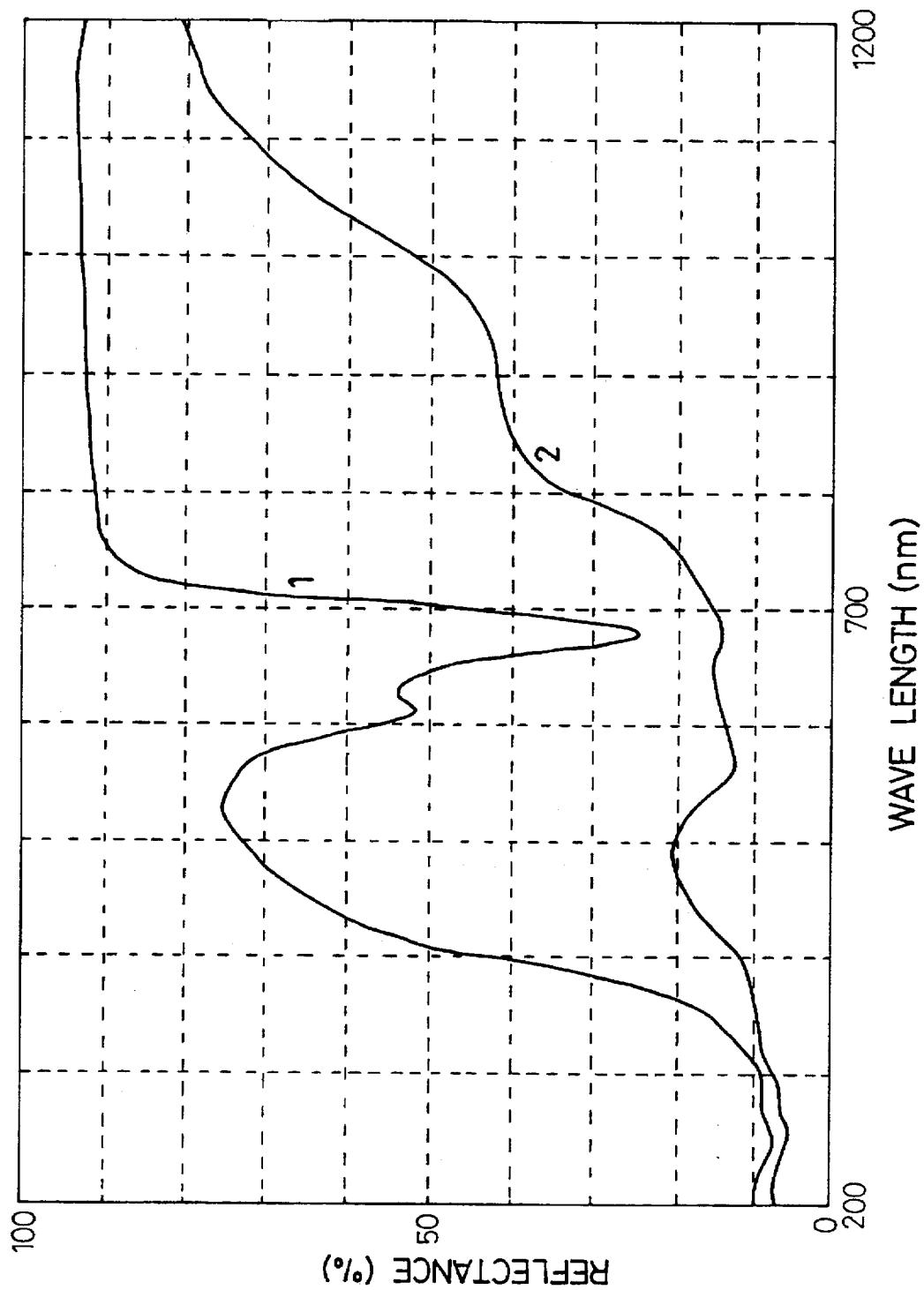
FIG. 3 shows the reflection spectra of the color images on heat-sensitive recording materials, and curves 1 and 2 denote the reflection spectra of the color images on the heat-sensitive recording materials obtained in Example 42 and Example 44, respectively.

The thus obtained heat-sensitive recording material was brought into contact with a hot iron at 200° C. for 3 seconds to form a color image all over the surface of the recording material. The reflection spectrum of this color image is shown as a curve 1 in FIG. 3.

EXAMPLE 43

(Preparation of heat-sensitive recording material)

Figure 4:
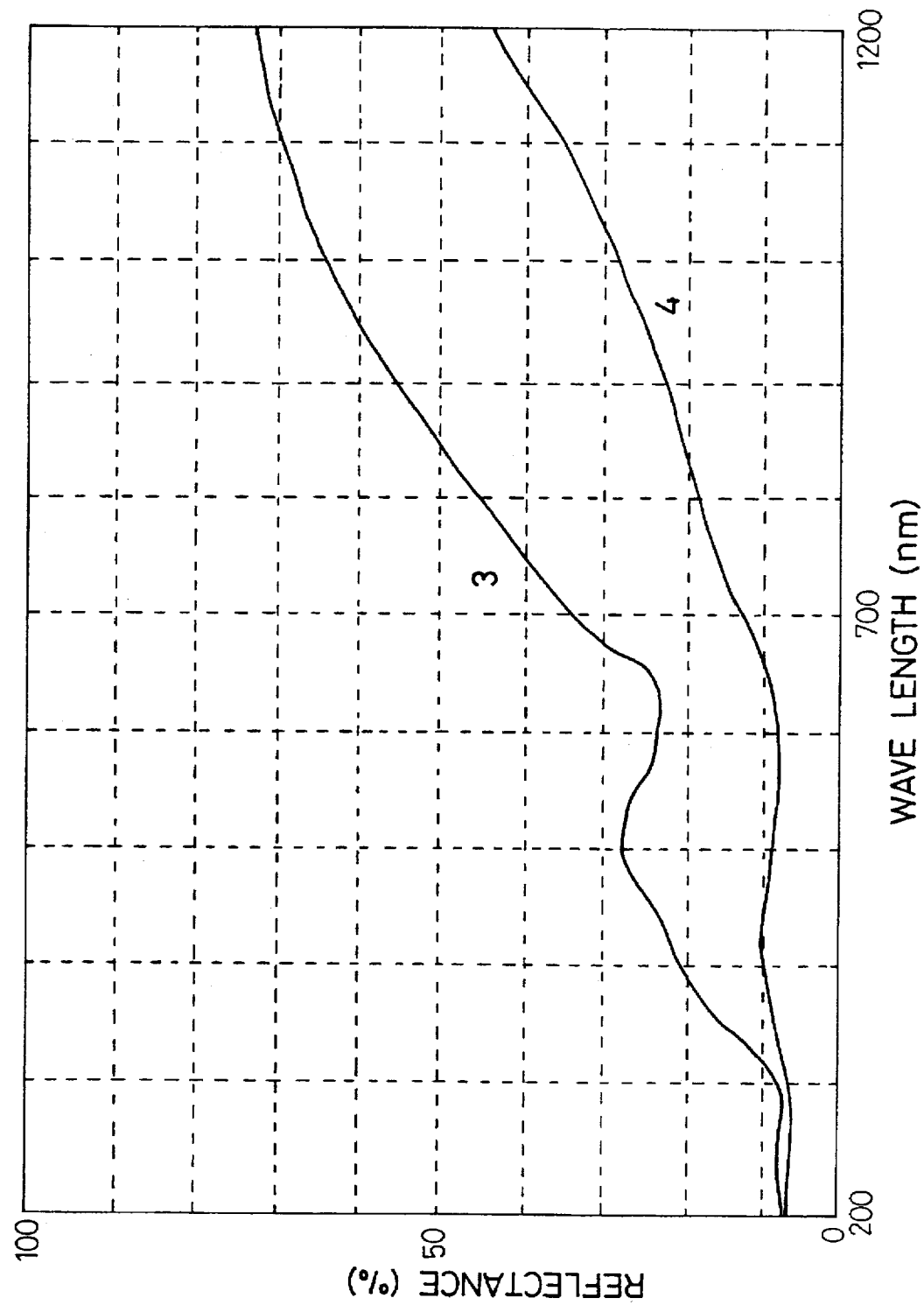
FIG. 4 shows the reflection spectra of the color images on heat-sensitive recording materials, and curves 3 and 4 denote the reflection spectra of the color images on the heat-sensitive recording materials obtained in Example 43 and Example 45, respectively.

The same procedure as in Example 42 was carried out except that 1,3-diiminoisoindoline benzoate obtained in Example 1 was replaced with 1,3-diimino-4,7-diaza-5,6-dimethylisoindoline benzoate obtained in Example 16, to obtain a heat-sensitive recording material and a color image all over the surface of the recording material. The reflection spectrum of this color image is shown as a curve 3 in FIG. 4.

EXAMPLE 44

(Preparation of heat-sensitive recording material)

Each mixture having the following composition was milled by a sand mill so that an average particle diameter might be 1.5 μm or less, to obtain each dispersion.

| Dispersion of carboxylate | |
|---|---|
| 1,3-diiminoisoindoline benzoate | 1 part |
| 5% aqueous polyvinyl alcohol solution | 10 parts |
| Dispersion of carbonyl compound | |
| 2,5-diethoxycarbonyl-1,4-cyclohexanedione | 1 part |
| 5% aqueous polyvinyl alcohol solution | 10 parts |

Heat-sensitive Coating Solution

To the mixture of the two total dispersions prepared above was added 8 parts of a 60% aqueous light-duty calcium carbonate dispersion, and the solution was then sufficiently mixed to obtain a heat-sensitive coating solution.

This heat-sensitive coating solution was applied onto a fine paper by the use of a Meyer bar No. 10 so that the amount of the coating solution might be 6 g/m² in terms of a solid content, and then dried to obtain a heat-sensitive recording material.

The thus obtained heat-sensitive recording material was brought into contact with a hot iron at 200° C. for 3 seconds to form a color image all over the surface of the recording material. The reflection spectrum of this color image is shown as a curve 2 in FIG. 3.

EXAMPLE 45

(Preparation of heat-sensitive recording material)

The same procedure as in Example 44 was carried out except that 1,3-diiminoisoindoline benzoate was replaced with 1,3-diimino-4,7-diaza-5,6-dimethylisoindoline benzoate obtained in Example 16, to obtain a heat-sensitive recording material and a color image all over the surface of the recording material. The reflection spectrum of this color image is shown as a curve 4 in FIG. 4.

EXAMPLE 46

(Preparation of heat-sensitive recording material)

Figure 5:
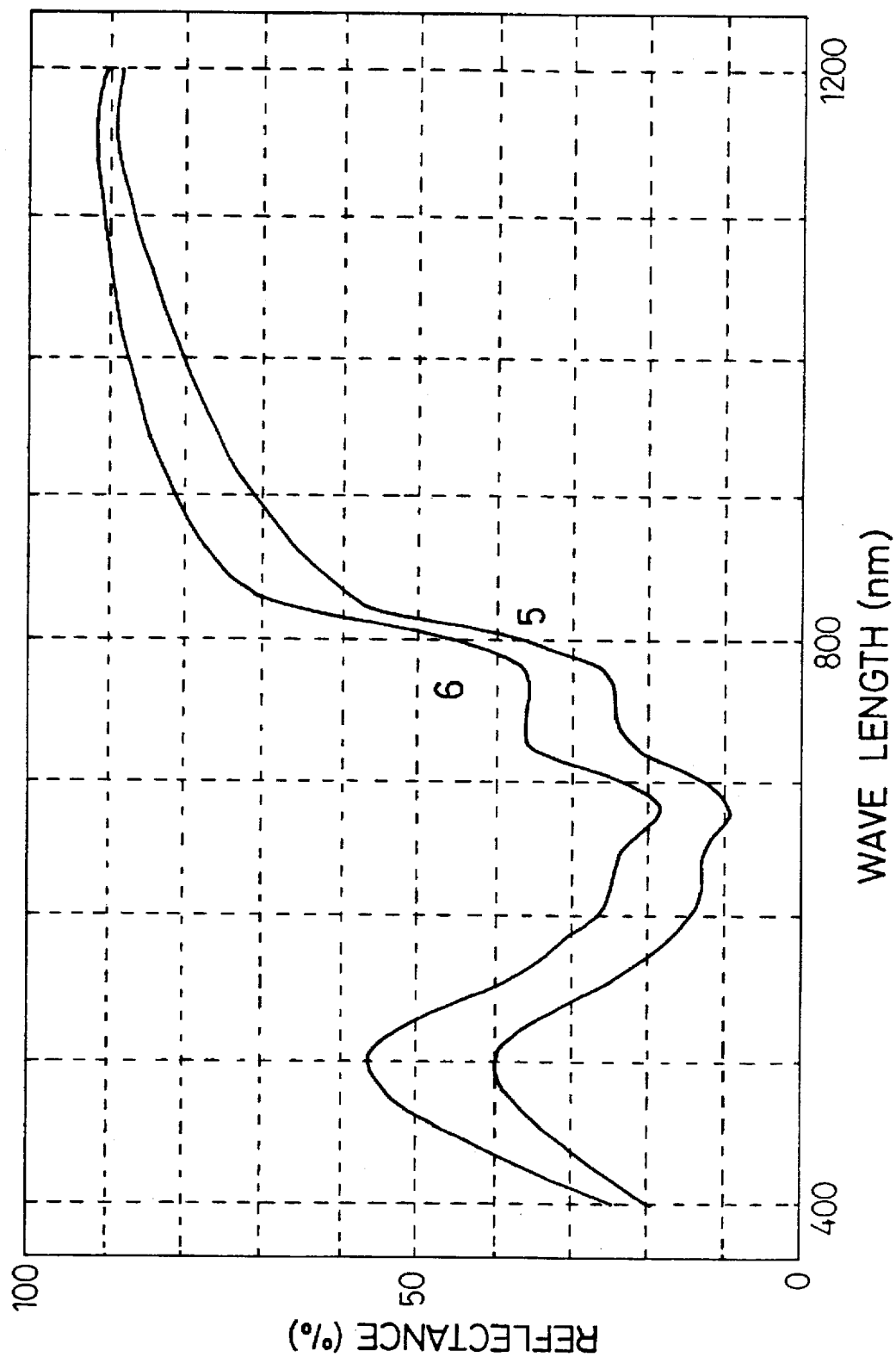
FIG. 5 shows the reflection spectra of the color images on heat-sensitive recording materials, and curves 5 and 6 denote the reflection spectra of the color images on the heat-sensitive recording materials obtained in Example 46 and Example 47, respectively.

The same procedure as in Example 42 was carried out except that 1,3-diiminoisoindoline benzoate was replaced with 1,1-ethylenedioxy-3-iminoisoindoline orthotoluylate obtained in Example 27, to obtain a heat-sensitive recording material and a color image all over the surface of the recording material. The reflection spectrum of this color image is shown as a curve 5 in FIG. 5.

EXAMPLE 47

(Preparation of heat-sensitive recording material)

The same procedure as in Example 42 was carried out except that 1,3-diiminoisoindoline benzoate was replaced with 1,1-(1'-methylethylenedioxy)-3-iminoisoindoline paratoluylate obtained in Example 30, to obtain a heat-sensitive recording material and a color image all over the surface of the recording material. The reflection spectrum of this color image is shown as a curve 6 in FIG. 5.

EXAMPLE 48

(Preparation of heat-sensitive recording material)

Figure 6:
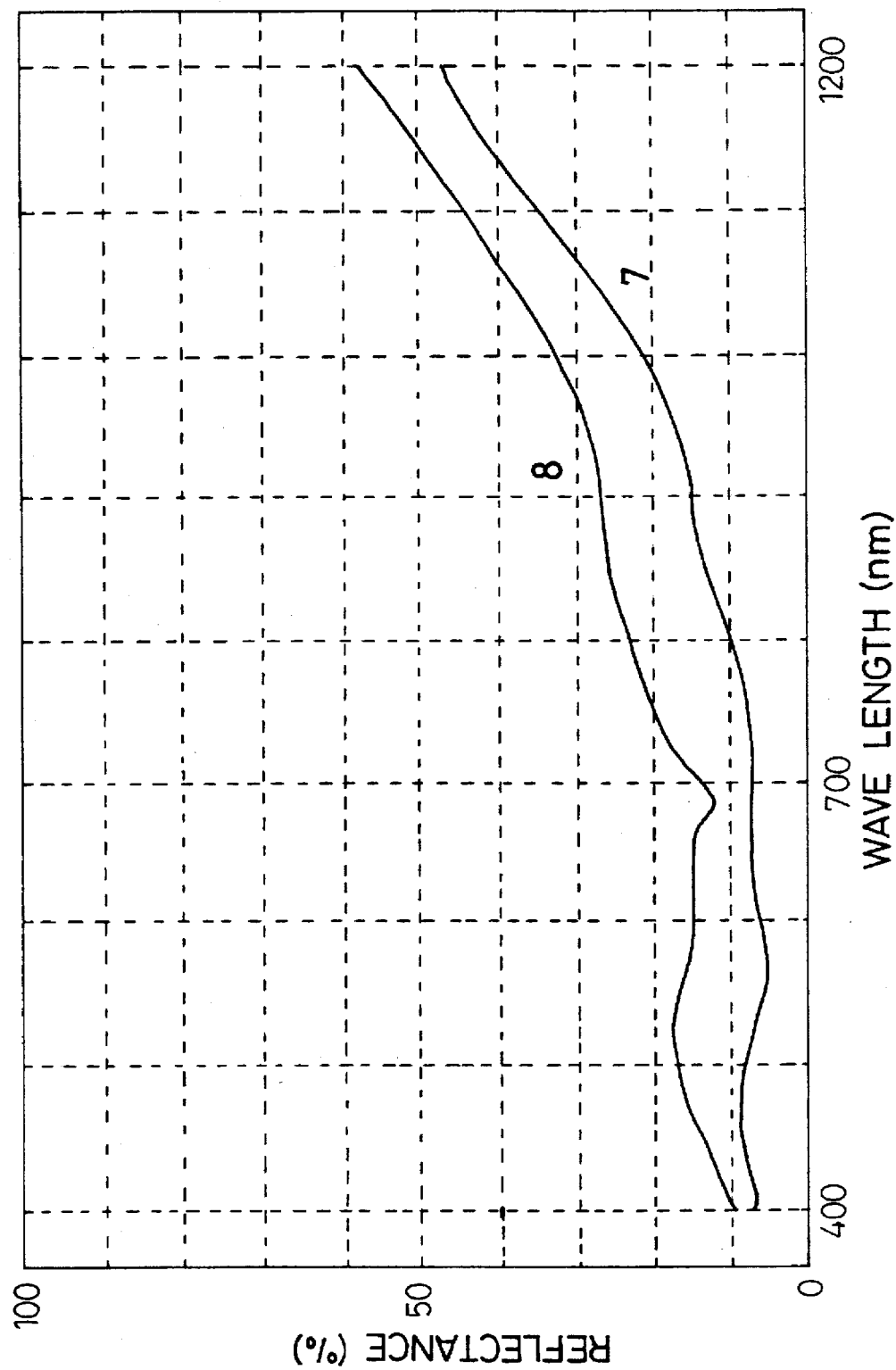
FIG. 6 shows the reflection spectra of the color images on heat-sensitive recording materials, and curves 7 and 8 denote the reflection spectra of the color images on the heat-sensitive recording materials obtained in Example 48 and Example 49, respectively.

The same procedure as in Example 44 was carried out except that 1,3-diiminoisoindoline benzoate was replaced with 1,1-dimethoxy-3-iminoisoindoline paratoluylate obtained in Example 17, to obtain a heat-sensitive recording material and a color image all over the surface of the recording material. The reflection spectrum of this color image is shown as a curve 7 in FIG. 6.

EXAMPLE 49

(Preparation of heat-sensitive recording material)

The same procedure as in Example 44 was carried out except that 1,3-diiminoisoindoline benzoate was replaced with 1,1-(1',1',3'-trimethyltrimethylenedioxy)-3-iminoisoindoline paratoluylate obtained in Example 37, to obtain a heat-sensitive recording material and a color image all over the surface of the recording material. The reflection spectrum of this color image is shown as a curve 8 in FIG. 6.

EXAMPLES 50 to 67

(Preparation of heat-sensitive recording materials)

The same procedure as in Example 44 was carried out except that carboxylates obtained in examples or reference examples were used as carboxylates in place of 1,3-diiminoisoindoline benzoate and carbonyl compounds mentioned in Table 4 were used as carbonyl compounds in place of 2,5-diethoxycarbonyl-1,4-cyclohexanedione, to obtain a heat-sensitive recording material and a color image all over the surface of the recording material. The results of these examples are all shown in Table 4.

TABLE 4

| | Carboxylic acid | Carbonyl compound | Coloring hue |
|---|---|---|---|
| Example 50 | Example 2 | 2,5-Diethoxycarbonyl-1,4-cyclohexanedione | Black |
| Example 51 | Ref. Ex. 11 | 2,5-Diethoxycarbonyl-1,4-cyclohexanedione | Black |
| Example 52 | Example 10 | 2,5-Dioctyloxycarbonyl-1,4-cyclohexanedione | Green |
| Example 53 | Ref. Ex. 15 | 2,5-Diethoxycarbonyl-1,4-cyclohexanedione | Greenish black |
| Example 54 | Ref. Ex. 16 | 1,4-Cyclohexanedione | Dark navy blue |
| Example 55 | Ref. Ex. 17 | 2,5-Dibutoxycarbonyl-1,4-cyclohexanedione | Blackish green |
| Example 56 | Ref. Ex. 18 | 1,2-Diacetylbenzene | Black |
| Example 57 | Ref. Ex. 19 | 1,4-Cyclohexanedione | Blackish |
| Example 58 | Example 13 | 1,4-Cyclohexanedione | Blackish green |
| Example 59 | Example 14 | 2,5-Dimethoxycarbonyl-1,4-cyclohexanedione | Blackish green |
| Example 60 | Example 15 | 2,5-Dihydroxypropoxycarbonyl 1,4-cyclohexanedione | Green |
| Example 61 | Ref. Ex. 20 | 1,1,2,2-Tetraacetylethane | Blackish green |
| Example 62 | Example 21 | 1,4-Cyclohexanedione | Dark navy |

TABLE 4-continued

| | Carboxylic acid | Carbonyl compound | Coloring hue |
|---|---|---|---|
| Example 63 | Example 25 | 2,5-Dimethoxycarbonyl-1,4-cyclohexanedione | blue Dark navy blue |
| Example 64 | Example 29 | 2,5-Dibutoxycarbonyl-1,4-cyclohexanedione | Dark navy blue |
| Example 65 | Example 31 | 1,1,2,2-Tetraacetylethane | Dark green |
| Example 66 | Example 35 | 2,5 Dioctylcarbonyl-1,4-cyclohexanedione | Dark navy blue |
| Example 67 | Example 32 | 1,2-Diacetylbenzene | Black |

COMPARATIVE EXAMPLE 1

(Preparation of heat-sensitive recording material)

Each mixture having the following composition was milled by a sand mill so that an average particle diameter might be 1.5 μm or less, to obtain each dispersion.

| Dispersion of color former | |
|---|---|
| 2-anilino-3-methyl-6-di-n-butylaminofluoran | 1 part |
| 5% agueous polyvinyl alcohol solution | 10 parts |
| Dispersion of developer | |
| Bisphenol A | 1 part |
| 5% aqueous polyvinyl alcohol solution | 10 parts |

Heat-sensitive Coating Solution

To the mixture of the two total dispersions prepared above was added 8 parts of a 60% aqueous light-duty calcium carbonate dispersion, and the solution was then sufficiently mixed to obtain a heat-sensitive coating solution.

This heat-sensitive coating solution was used and the same operation as in Example 42 was carried out to obtain a heat-sensitive recording material and a color image all over the surface of the recording material.

COMPARATIVE EXAMPLE 2

(Preparation of heat-sensitive recording material)

Each mixture having the following composition was milled by a sand mill so that an average particle diameter might be 1.5 μm or less, to obtain each dispersion.

| Dispersion of imino compound | |
|---|---|
| 1,3-diimino-4,5,6,7-tetrachloroisoindoline | 1 part |
| 5% aqueous polyvinyl alcohol solution | 10 parts |
| Dispersion of isocyanate | |
| 4,4',4"-triisocyanato-2,5-dimethoxy-triphenylamine | 1 part |
| 5% aqueous polyvinyl alcohol solution | 10 parts |

Heat-sensitive Coating Solution

To the mixture of the two total dispersions prepared above was added 8 parts of a 60% aqueous light-duty calcium carbonate dispersion, and the solution was then sufficiently mixed to obtain a heat-sensitive coating solution.

This heat-sensitive coating solution was used and the same operation as in Example 42 was carried out to obtain a heat-sensitive recording material and a color image all over the surface of the recording material.

COMPARATIVE EXAMPLE 3

(Preparation of heat-sensitive recording material)

Each mixture having the following composition was milled by a sand mill so that an average particle diameter might be 1.5 μm or less, to obtain each dispersion.

| Dispersion of imino compound | |
|---|---|
| 1,1-dimethoxy-3-iminoisoindoline | 1 part |
| 5% aqueous polyvinyl alcohol solution | 10 parts |
| Dispersion of carbonyl compound | |
| 2,5-diethoxycarbonyl-1,4-cyclohexanedione | 1 part |
| 5% aqueous polyvinylalcohol solution | 10 parts |

Heat-sensitive Coating Solution

To the total mixture of two dispersions prepared above was added 8 parts of a 60% aqueous light-duty calcium carbonate dispersion, and the solution was then sufficiently mixed to obtain a heat-sensitive coating solution. This heat-sensitive coating solution was used and the same operation as in Example 42 was carried out to obtain a heat-sensitive recording material and a color image all over the surface of the recording material.

COMPARATIVE EXAMPLE 4

(Preparation of heat-sensitive recording material)

Each mixture having the following composition was milled by a sand mill so that an average particle diameter might be 1.5 μm or less, to obtain each dispersion.

| Dispersion of imino compound | |
|---|---|
| 1,3-diimino-4,5,6,7-tetrachloroisoindoline | 1 part |
| 5% aqueous polyvinyl alcohol solution | 10 parts |
| Dispersion of carbonyl compound | |
| 1,4-cyclohexanedione | 1 part |
| 5% aqueous polyvinyl alcohol solution | 10 parts |

Heat-sensitive Coating Solution

To the mixture of the two total dispersions prepared above was added 8 parts of a 60% aqueous light-duty calcium carbonate dispersion, and the solution was then sufficiently mixed to obtain a heat-sensitive coating solution.

This heat-sensitive coating solution was used and the same operation as in Example 42 was carried out to obtain a heat-sensitive recording material and a color image all over the surface of the recording material.

(Evaluation)

For each of the heat-sensitive recording materials obtained in the examples and the comparative examples, the stability of a background (an uncolored portion) and the color image was inspected, and the results are shown in Tables 5 and 6.

(1) Storage stability of background

A survival ratio (a white degree maintenance ratio) represented by the following formula was calculated, and the storage stability of the background was evaluated from the value of the survival ratio:

The survival ratio (%)={(the white degree of the background after a test)/(the white degree of the background before the test)}×100.

The white degree was measured by the use of a color difference meter Σ80 (made by Nippon Denshoku Co., Ltd.) and an amber filter.

27

Test of Light Resistance (A in Table 5)

After the uncolored portion of each recording material was irradiated with a fluorescent lamp of 20,000 lux for 10 days, the white degree was measured to obtain the survival ratio.

Test of Heat Resistance (B in Table 5)

After the uncolored portion of each recording material was maintained at 60° C. for 24 hours, the white degree was measured to obtain the survival ratio.

Test of Moist Heat Resistance (C in Table 5)

After the uncolored portion of each recording material was maintained at 40° C. and a relative humidity of 90% for 24 hours, the white degree was measured to obtain the survival ratio.

Test of DOP Stability (D in Table 5)

A paper coated with a capsule coating solution containing dioctyl phthalate was superposed upon the uncolored portion of each recording material, and a press roll was then passed thereon. After the coated paper was maintained at 25° C. for 1 week, the white degree was measured to obtain the survival ratio.

Test of Vinyl Chloride Film Stability (E in Table 5)

High-wrap (trade name, made by Mitsui Toatsu Chemicals, Inc.) was brought into contact with the uncolored portion of each recording material, and a load of 100 $g/cm^2$ was then applied thereto. After the application of this load was maintained at 40° C. for 24 hours, the white degree was measured to obtain the survival ratio.

TABLE 5

| | White degree | Background stability (survival ratio: %) | | | | |
|---|---|---|---|---|---|---|
| | | A | B | C | D | E |
| Ex. 42 | 84.1 | 99 | 100 | 100 | 98 | 100 |
| Ex. 43 | 83.3 | 98 | 97 | 98 | 98 | 100 |
| Ex. 44 | 83.5 | 98 | 99 | 97 | 98 | 100 |
| Ex. 45 | 82.4 | 98 | 97 | 97 | 98 | 100 |
| Ex. 51 | 82.0 | 98 | 99 | 98 | 99 | 100 |
| Ex. 52 | 84.4 | 98 | 99 | 97 | 98 | 100 |
| Comp. 1 | 84.6 | 89 | 94 | 96 | 91 | 97 |
| Comp. 2 | 82.0 | 63 | 77 | 94 | 45 | 68 |

(2) Stability of color image

A survival image ratio (an optical density maintenance ratio) represented by the following formula was calculated, and the stability of a color image was evaluated on the basis of the value of the survival image ratio:

The survival image ratio (%)={(the density of the color image after a test)/(the density of the color image before the test)}×100

The density was an OD value measured by the use of a Macbeth densitometer (TR-254 model) and an amber filter.

Test of Light Resistance (A in Table 6)

Light resistance was denoted by the survival image ratio after the color image of each recording material was irradiated with an ultraviolet carbon arc (made by Suga Test Machine Co., Ltd.) for 24 hours.

Test of Moist Heat Resistance (B in Table 6)

After the color image of each recording material was maintained at 60° C. and a relative humidity of 90% for 24 hours, the density was measured to obtain the survival image ratio.

Test of DOP Stability (C in Table 6)

A paper coated with a capsule coating solution containing dioctyl phthalate was superposed upon the color image of each recording material, and a press roll was then passed thereon. After the coated paper was maintained at 25° C. for 1 week, the density was measured to obtain the survival ratio.

28

Test of Vinyl Chloride Film Stability (D in Table 6)

High-wrap (trade name, made by Mitsui Toatsu Chemicals, Inc.) was brought into contact with the color image of each recording medium, and a load of 100 $g/cm^2$ was then applied thereto. After the application of this load was maintained at 40° C. for 24 hours, the density was measured to obtain the survival ratio.

TABLE 6

| | Concentration | Image stability (survival ratio: %) | | | |
|---|---|---|---|---|---|
| | | A | B | C | D |
| Ex. 42 | 0.74 | 98 | 100 | 100 | 100 |
| Ex. 43 | 0.93 | 99 | 100 | 100 | 100 |
| Ex. 44 | 1.26 | 98 | 100 | 100 | 100 |
| Ex. 45 | 1.38 | 100 | 100 | 100 | 100 |
| Ex. 51 | 1.23 | 98 | 100 | 100 | 100 |
| Ex. 52 | 1.29 | 99 | 100 | 100 | 100 |
| Ex. 63 | 1.30 | 100 | 100 | 100 | 100 |
| Ex. 64 | 1.29 | 100 | 100 | 100 | 100 |
| Ex. 65 | 1.28 | 99 | 100 | 100 | 100 |
| Ex. 66 | 1.34 | 100 | 100 | 100 | 100 |
| Comp. 1 | 1.37 | 11 | 85 | 93 | 15 |
| Comp. 2 | 1.06 | 85 | 100 | 100 | 97 |
| Comp. 3 | 0.08 | — | — | — | — |
| Comp. 4 | 0.05 | — | — | — | — |

In Comparative Example 3, 1,1-dimethoxy-3-iminoisoindoline was hydrolyzed in an aqueous polyvinyl alcohol solution, and so that an evaluation was not carried out. Furthermore, in Comparative Example 4, color was not developed even when heat was applied, so that an evaluation could not be made.

Next, reference will be made to heat-sensitive recording materials which comprise a heat-sensitive recording layer containing a carboxylate and an aromatic isocyanate of the present invention.

EXAMPLE 68

Each mixture having the following composition was milled and dispersed by a sand mill so that an average particle diameter might be several micrometers, to obtain a carboxylate dispersion (hereinafter referred to as "the dispersion A") and an aromatic isocyanate dispersion (hereinafter referred to as "the dispersion B").

| Dispersion A | |
|---|---|
| 1,3-diiminoisoindoline orthotoluylate | 1 part |
| 5% aqueous polyvinyl alcohol solution | 10 parts |
| Dispersion B | |
| 4,4',4"-triisocyanato-2,5-dimethoxy-triphenylamine | 1 part |
| 5% aqueous polyvinyl alcohol solution | 10 parts |

Heat-sensitive Coating Solution

The dispersions prepared above were mixed with each other at a ratio of the dispersion A:the dispersion B=1:1, and 1 part of a 60% aqueous light-duty calcium carbonate dispersion was added to 6 parts of the resultant mixture. Afterward, the solution was sufficiently mixed to obtain a heat-sensitive coating solution.

This heat-sensitive coating solution was applied onto a fine paper by the use of a Meyer bar No. 10 so that the amount of the coating solution might be 6 $g/m^2$ in terms of a solid content, and then dried to obtain a heat-sensitive recording material.

The thus obtained heat-sensitive recording material was brought into contact with a hot iron at 200° C. for 3 seconds, so that a violet-like brown color was developed.

EXAMPLE 69

Each mixture having the following composition was milled and dispersed by a sand mill so that an average particle diameter might be several micrometers, to obtain a dispersion A, a dispersion B and a carbonyl compound dispersion (hereinafter referred to as "the dispersion C").

| Dispersion A | |
|---|---|
| 1,3-diiminoisoindoline benzoate | 1 part |
| 5% aqueous polyvinyl alcohol solution | 10 parts |
| Dispersion B | |
| 4,4',4"-triisocyanato-2,5-dimethoxytriphenylamine | 1 part |
| 5% aqueous polyvinyl alcohol solution | 10 parts |
| Dispersion C | |
| 2,5-diethoxycarbonyl-1,4-dicarboxylic acid | 1 part |
| 5% aqueous polyvinyl alcohol solution | 10 parts |

Heat-sensitive Coating Solution

The dispersions prepared above were mixed with each other at a ratio of the dispersion A:the dispersion B:the dispersion C=2:1:1, and 1 part of a 60% aqueous light-duty calcium carbonate dispersion was added to 6 parts of the resultant mixture. Afterward, the solution was sufficiently mixed to obtain a heat-sensitive coating solution.

This heat-sensitive coating solution was applied onto a fine paper by the use of a Meyer bar No. 10 so that the amount of the coating solution might be 6 g/m$^2$ in terms of a solid content, and then dried to obtain a heat-sensitive recording material.

The thus obtained heat-sensitive recording material was brought into contact with a hot iron at 150° C. for 3 seconds, so that black color was developed.

EXAMPLES 70 to 103

The same procedure as in Example 68 was carried out except that 1,3-diiminoisoindoline orthotoluylate and 4,4',4"-triisocyanate-2,5-dimethoxytriphenylamine were placed with carboxylates and aromatic isocyanates shown in Table 7, to prepare heat-sensitive recording materials, and thermal color development was then carried out by the same operation as in Example 68. Coloring hues are all shown in Table 7.

TABLE 7

| Ex. No. | Carboxylate | Aromatic isocyanate | Coloring hue |
|---|---|---|---|
| 70 | 1,3-Diiminoisoindoline benzoate | 2,5-Diethoxybenzene-1,4-diisocyanate | Light brown |
| 71 | 1,3-Diiminoisoindoline butyrate | 2,6-Dichlorophenyl-isocyanate | Yellowish green |
| 72 | 1,3-Diiminoisoindoline acetate | p-Chlorophenyl-isocyanate | Yellow |
| 73 | 1,3-Diiminoisoindoline p-chlorobenzoate | p-Phenylenediisocyanate | Orange |
| 74 | 1,3-Diiminoisoindoline m-chlorobenzoate | o-Phenylenediisocyanate | Yellow |
| 75 | 1,3-Diiminoisoindoline salicylate | Chlorobenzene-2,5-diisocyanate | Orange |
| 76 | 1,3-Diiminoisoindoline phenoxyacetate | 2,5-Diethoxybenzene-1,4-diisocyanate | Orange |
| 77 | 1,3-Diiminoisoindoline oleate | 2,5-Dimethoxybenzene-1,4-diisocyanate | Dark red |
| 78 | 1,3-Diiminoisoindoline phenylalanine salt | 2,5-Diethoxybenzene-1,4-diisocyanate | Dark red |
| 79 | 1,3-Diiminoisoindoline lactate | 3,3'-Dichloro-4,4'-diphenyldiisocyanate | Orange |
| 80 | 1,3-Diiminoisoindoline chloroacetate | 3,3'-Dimethyl-4,4'-diphenyldiisocyanate | Red |
| 81 | 1,3-Diiminoisoindoline pivalate | 3,3'-Dimethoxy-4,4'-diphenyldiisocyanate | Red |
| 82 | 1,3-Diiminoisoindoline methoxyacetate | 4,4'-Diphenylmethane diisocyanate | Yellowish green |
| 83 | 1,3-Diiminoisoindoline laurate | 4,4'-Benzophenone diisocyanate | Orange |
| 84 | 1,3-Diiminoisoindoline succinic acid monoethyl ester salt | Diphenylsulphone-4,4'-diisocyanate | Yellow |
| 85 | 1,3-Diiminoisoindoline succinic acid monooctyl ester salt | 4,4'-Benzanilidodiisocyanate | Light brown |
| 86 | 1,3-Diiminoisoindoline succinic acid stearyl ester salt | 4,4'-Azobenzenediisocyanate | Orange |
| 87 | 1,3-Diiminoisoindoline p-toluylate | 2,7-Fluorene diisocyanate | Light brown |
| 88 | 1,3-Diiminoisoindoline benzoylbenzoate | 1,5-Naphthalene diisocyanate | Orange |
| 89 | 1,3-Diimino-4-(2,4-dimethylpentoxy)isoindoline p-toluylate | p-Phenylene diisocyanate | Light brown |
| 90 | 1,3-Diimino-4-ethoxyisoindoline p-toluylate | 2,5-Dimethoxybenzene-1,4-diisocyanate | Dark red |
| 91 | 1,3-Diimino-5-t-butylisoindoline acetate | 4,4'-Benzanilide diisocyanate | Light brown |
| 92 | 1,3-Diimino-6-t-butylbenzioindoline methoxyacetate | 1,5-Naphthalene diisocyanate | Liver brown |
| 93 | 1,3-Diimino-6-chlorobenzisoindoline methoxyacetate | 2,7-Fluorene diisocyanate | Brown |
| 94 | 1,3-Diimino-4-nitroisoindoline anisate | 3,3'-Dimethyl-4,4'-diphenyldiisocyanate | Red |
| 95 | 1,3-Diimino-5,7-dihydroxyisoindoline p-chlorobenzoate | 4,4'-Diphenylmethane | Yellow |
| 96 | 1,3-Diimino-5-heptylthioisoindoline p-chlorobenzoate | 4,4'-Diphenylmethane diisocyanate | Yellow |
| 97 | 1,3-Diimino-5,6-dimethyl 4,7-diazaisoindoline benzoate | 2,5-Diethoxybenzene-1,4-diisocyanate | Dark red |
| 98 | 1,3-Diimino-4-nitroisoindoline anisate | o-Phenylene diisocyanate | Yellow |
| 99 | 1,3-Diimino-5-aminoisoindoline benzoate | 2,5-Dichlorobenzene-1,4-diisocyanate | Yellow |
| 100 | 1,3-Diimino-5-diimethylaminoisoindoline benzoate | p-Phenylene diisocyanate | Yellow |
| 101 | 1,3-Diimino-5-trimethylsilylisoindoline m-toluylate | p-Chlorophenyl-isocyanate | Yellow |
| 102 | 1,3-Diimino-5-trifluoromethylisoindoline acetate | 2,5-Dimethylbenzene-1,4-diisocyanate | Orange |
| 103 | 1,3-Diimino-5-trimethylsilyloxyisoindoline butyrate | 3,3'-Dimethyl-4,4'-diphenyldiisocyanate | Red |

COMPARATIVE EXAMPLE 5

Each mixture having the following composition was milled and dispersed by a sand mill so that an average particle diameter might be several micrometers, to obtain a dyestuff dispersion (hereinafter referred to as "the dispersion D") and a developer dispersion (hereinafter referred to as "the dispersion E").

| Dispersion D | |
|---|---|
| 2-anilino-3-methyl-6-di-n-butylaminofluoran | 1 part |
| 5% aqueous polyvinyl alcohol solution | 10 parts |
| Dispersion E | |
| Bisphenol A | 1 part |
| 5% aqueous polyvinyl alcohol solution | 10 parts |

Heat-sensitive Coating Solution

The dispersions prepared above were mixed with each other at a ratio of the dispersion D:the dispersion E=1:2, and 1 part of a 60% aqueous light-duty calcium carbonate dispersion was added to 6 parts of the resultant mixture. Afterward, the solution was sufficiently mixed to obtain a heat-sensitive coating solution.

This heat-sensitive coating solution was applied onto a fine paper by the use of a Meyer bar No. 10 so that the amount of the coating solution might be 6 g/m² in terms of a solid content, and then dried to obtain a heat-sensitive recording material.

The same operation as in Example 1 was carried out to thermally develop a color, so that a black image was obtained.

COMPARATIVE EXAMPLE 6

The same procedure as in Example 68 was carried out except that 1,3-diiminoisoindoline orthotoluylate was replaced with 1,3-diiminoisoindoline. As a result, a light dark brown image was obtained.

(Evaluation)

For each of the heat-sensitive recording materials obtained in Examples 68 and 69 and Comparative Examples 5 and 6, the stability of a background and the color image was inspected, and the results are shown in Tables 8 and 9.

(1) Stability of background

A survival ratio (a white degree maintenance ratio) represented by the following formula was calculated, and storage stability was evaluated on the basis of the value of the survival ratio:

The survival ratio (%)={(the white degree of the background after a test)/(the white degree of the background before the test)}×100.

The white degree was measured by the use of a color difference meter Σ80 (made by Nippon Denshoku Co., Ltd.) and an amber filter.

Test of Light Resistance (A in Table 8)

After the uncolored portion of each recording material was irradiated with a fluorescent lamp of 20,000 lux for 10 days, the white degree was measured to obtain the survival ratio.

Test of Heat Resistance (B in Table 8)

After the uncolored portion of each recording material was maintained at 60° C. for 24 hours, the white degree was measured to obtain the survival ratio.

Test of Moist Heat Resistance (C in Table 8)

After the uncolored portion of each recording material was maintained at 40° C. and a relative humidity of 90% for 24 hours, the white degree was measured to obtain the survival ratio.

Test of DOP Stability (D in Table 8)

A paper coated with a capsule coating solution containing dioctyl phthalate was superposed upon the uncolored portion of each recording material, and a press roll was then passed thereon. After the coated paper was maintained at 25° C. for 1 week, the white degree was measured to obtain the survival ratio.

Coloring Performance after Test of Moist Heat Resistance

The color development state of the recording materials was inspected, and a case where the color was developed is represented by "O", and a case where the color was not developed is represented by "X".

TABLE 8

| | White degree | Background stability (survival ratio: %) | | | | Coloration after heat moisture resistance test |
|---|---|---|---|---|---|---|
| | | A | B | C | D | |
| EX. 68 | 83.5 | 95 | 99 | 99 | 100 | O |
| Ex. 69 | 84.3 | 96 | 98 | 99 | 100 | O |
| Comp. 5 | 85.8 | 89 | 94 | 97 | 91 | O |
| Comp. 6 | 83.0 | 63 | 68 | 93 | 45 | X |

(2) Stability of color image

A survival ratio (an optical density maintenance ratio) represented by the following formula was calculated, and the storage of a color image was evaluated on the basis of the value of the survival image ratio:

The survival ratio (%)={(the density of the color image after a test)/(the density of the color image before the test)}×100

The density was an OD value measured by the use of a Macbeth densitometer (TR-254 model) and an amber filter.

Test of Light Resistance (A in Table 9)

Light resistance was denoted by the survival ratio after the color image on the recording material was irradiated with an ultraviolet carbon arc (made by Suga Test Machine Co., Ltd.) for 8 hours.

Test of Moist Heat Resistance (B in Table 9)

After the color image of each recording material was maintained at 60° C. and a relative humidity of 90% for 24 hours, the density was measured to obtain the survival ratio.

Test of DOP Stability (C in Table 9)

A paper coated with a capsule coating solution containing dioctyl phthalate was superposed upon the color image of each recording material, and a press roll was then passed thereon. After the coated paper was maintained at 25° C. for 1 week, the density was measured to obtain the survival ratio.

TABLE 9

| | Concentration | Image stability (survival ratio: %) | | |
|---|---|---|---|---|
| | | A | B | C |
| Ex. 69 | 1.20 | 99 | 100 | 100 |
| Ex. 69 | 1.23 | 100 | 100 | 100 |
| Comp. 5 | 1.37 | 59 | 84 | 93 |
| Comp. 6 | 0.36 | 84 | 87 | 95 |

Next, reference will be made to heat-sensitive recording labels which comprise a heat-sensitive recording layer containing a carboxylate of the present invention.

EXAMPLE 104

Each of solutions A and C having the following compositions was milled by a sand mill so that an average particle diameter might be 3 μm, to obtain dispersions. A heat-sensitive coating solution was obtained only by mixing and stirring.

| Dispersion A | |
|---|---|
| 1,3-diiminoisoindoline metatoluylate | 2 parts |
| 5% aqueous polyvinyl alcohol solution | 1 part |
| Water | 8 parts |
| Dispersion C | |
| Diethylsuccinyl succinate | 2 parts |
| 5% aqueous polyvinyl alcohol solution | 1 part |
| Water | 6 parts |

Heat-sensitive Coating Solution

The solutions A and C, fine particles of anhydrous silica and a 10% aqueous polyvinyl alcohol solution were sufficiently mixed at a ratio of the solution A: the solution C: the fine particles of anhydrous silica: the 10% aqueous polyvinyl alcohol solution=5:5:2:4 to obtain a heat-sensitive coating solution.

Preparation of Heat-sensitive Recording Material

The heat-sensitive coating solution obtained above was applied onto one surface of a fine paper of 60 g/m² so that the amount of the coating solution might be 6 g/m2in terms of a solid content, followed by drying, to obtain a heat-sensitive recording material.

Preparation of Heat-sensitive Recording Label

A silicone release agent (trade name KS-770, made by Shinetsu Chemical Co., Ltd.) was applied onto a glassine paper of 70 g/m² so that the amount of the silicone release agent might be 0.9 g/m² in terms of dry weight, followed by drying, to obtain a release sheet. Afterward, an acrylic adhesive (trade name Nicasol L-120, made by Nippon Carbide Industries Co., Ltd.) was applied onto the release layer of this release sheet by a roll coater so that the amount of the acrylic adhesive might be 25 g/m² in terms of dry weight, followed by drying, to form an adhesive layer. Next, a support of the heat-sensitive recording material was superposed upon this adhesive layer, and they were then pressed by a press roll to obtain a heat-sensitive recording label.

EXAMPLES 105 to 108

The same procedure as in Example 104 was carried out except that carboxylates and carbonyl compounds having a hydrogen atom at the α-position in Example 104 were replaced with compounds shown in Table 10, to obtain heat-sensitive recording labels.

| Ex. No. | Carboxylate | Carbonyl compound |
|---|---|---|
| 105 | 1,3-Diiminoisoindoline succinic acid mono-n-butyl ester salt | Di-n-butylsuccinylsuccinate |
| 106 | 1,3-Diiminoisoindoline succinic acid monobenzyl ester salt | 1,1,2,2-Tetraacetylethane |
| 107 | 1,3-Diiminoisoindoline phthalic acid monoethyl ester salt | 1,4-Cyclohexanedione |
| 108 | 1,3-Diiminoisoindoline ortho-toluylate | Bis(4-hydroxycyclohexyl)-succinylsuccinate |

COMPARATIVE EXAMPLE 7

The same procedure as in Example 104 was carried out except that 1,3-diiminoisoindoline metatoluylate was replaced with 2-anilino-3-methyl-6-di-n-butylaminofluoran and diethylsuccinyl succinate was replaced with bisphanol A, to obtain a heat-sensitive recording label.

(Evaluation)

The heat-sensitive recording labels obtained in Examples 104 to 108 and Comparative Example 7 were brought into contact with a hot iron at 160° C. for 3 seconds to obtain recorded images. For these recorded images, tests of light resistance, moist heat resistance, stability to DOP and stability to a vinyl chloride film were carried out, the results are shown in Table 11.

A survival image ratio (an optical density maintenance ratio) represented by the following formula was calculated, and the stability of a recorded image was evaluated on the basis of the value of the survival image ratio:

The survival image ratio (%)={(the density of the recorded image after a test)/(the density of the recorded image before the test)}×100

The density was an OD value measured by the use of a Macbeth densitometer (TR-254 model) and an amber filter.

Test of Light Resistance (A in Table 11)

Light resistance was denoted by the survival image ratio after the recorded image on each label was irradiated with an ultraviolet carbon arc (made by Suga Test Machine Co., Ltd.) for 8 hours.

Test of Moist Heat Resistance (B in Table 11)

After the recorded image on each label was maintained at 60° C. and a relative humidity of 90% for 24 hours, the density was measured to obtain the survival image ratio.

Test of DOP Stability (C in Table 11)

A paper coated with a capsule coating solution containing dioctyl phthalate was superposed upon the recorded image on each label, and a press roll was then passed thereon. After the recorded paper was maintained at 25° C. for 1 week, the density was measured to obtain the survival ratio.

Test of Vinyl Chloride Film Stability (D in Table 11)

High-wrap (trade name, made by Mitsui Toatsu Chemicals, Inc.) was brought into contact with the recorded image on each label, and a load of 100 g/cm² was then applied thereto. After the application of this load was maintained at 40° C. for 24 hours, the density was measured to obtain the survival ratio.

TABLE 11

| | Concentration | Image stability (survival ratio: %) | | | |
|---|---|---|---|---|---|
| | (OD value) | A | B | C | D |
| Ex. 104 | 1.21 | 98 | 100 | 100 | 100 |
| Ex. 105 | 1.16 | 97 | 100 | 100 | 100 |
| Ex. 106 | 1.14 | 97 | 100 | 100 | 100 |
| Ex. 107 | 1.18 | 98 | 100 | 100 | 100 |
| Ex. 108 | 1.21 | 98 | 100 | 100 | 100 |
| Comp. 7 | 1.37 | 59 | 84 | 93 | 93 |

Reference will be made to information recording cards which comprises a heat-sensitive recording layer containing a carboxylate of the present invention.

EXAMPLE 109

Each mixture having the following composition was milled for 1 hour by a sand mill to obtain a solution A and a solution C.

| Solution A | |
|---|---|
| 1,3-diiminoisoindoline metatoluylate | 1 part |
| Toluene | 9 parts |
| Solution C | |
| Diethylsuccinyl succinate | 1 part |
| Toluene | 9 parts |

Irreversible Heat-sensitive Coating Solution

Ten parts of the solution A were mixed with 10 parts of the solution C, and 1 part of a binder Almatics (trade name, made by Mitsui Toatsu Chemicals, Inc.) was added to the resultant mixture, followed by sufficient mixing, to obtain a heat-sensitive coating solution.

This heat-sensitive coating solution was applied onto a polyethylene terephthalate film having a thickness of 100 μm so that the amount of the coating solution might be 6 g/m² in terms of dry weight, followed by drying, to form an information recording card.

EXAMPLE 110

The following composition was sufficiently stirred and mixed to obtain a coating solution for a magnetic recording layer.

| Magnetic material composition | |
| --- | --- |
| Magnetic powder (17500e, barium ferrite) | 100 parts |
| Vinyl chloride-vinyl acetate copolymer (VAGF, made by Union Carbide Corp.) | 20 parts |
| Polyurethane resin (non-volatile matter = 30%) (Sunplen IB-114B, made by Mitsubishi Chemical Industries, Ltd.) | 15 parts |
| Dispersant (Garfac RE-610, Toho Chemical Industry Co., Ltd.) | 3 parts |
| Diluent (toluene:MEK:MIBK = 2:1:1) | 100 parts |

The obtained coating solution for the magnetic recording layer was applied as thick as 12 μm onto the back surface of a card obtained by the same procedure as in Example 109, subjected to magnetic field orientation in a horizontal magnetic field of about 3000 gauss, and then dried to obtain an information recording card.

On this card, irreversible heat-sensitive recording and reversible magnetic recording were possible.

EXAMPLE 111

The following resin matrix and an organic low-molecular weight substance were dissolved in tetrahydrofuran to prepare a coating solution for a reversible recording material.

| Composition of coating solution | |
| --- | --- |
| Polyvinyl acetal (Eslex KS-1, made by Sekisui Chemical Co., Ltd.) | 5 parts |
| Behenic acid | 3 parts |
| Tetrahydrofuran | 50 parts |

The obtained coating solution was applied as thick as 15 μm onto the back surface of a card obtained by the same procedure as in Example 109, followed by drying, to obtain an information recording card.

On the reversible recording portion of this card, printing was made by the use of a thermal head having an application energy of 1.3 joules/cm², and as a result, it was apparent that the printing was possible. The print could be erased with a hot stamp at 80° C., so that the recording portion returned to a white state. Furthermore, this operation was repeated 500 times, but the same white degree as in the first printing could be maintained.

EXAMPLE 112

Each mixture having the following composition was milled for 1 hour by a sand mill to obtain solutions F and G.

| Solution F (leuco-pigment dispersion) | |
| --- | --- |
| 2-anilino-3-methyl-6-(N-ethyl-N-toluylamino)fluoran | 5 parts |
| Polyvinylbutyral | 1 part |
| Toluene | 20 parts |
| Solution G (developer dispersion) | |
| Stearylamine gallate | 1 part |
| Fine powder of silicone resin | 1 part |
| Polyvinylbutyral | 1 part |
| Toluene | 4 parts |

Reversible Heat-sensitive Coating Solution

One part of the solution F was sufficiently mixed with 5 parts of the solution G to obtain a reversible heat-sensitive coating solution.

This reversible heat-sensitive coating solution was applied as thick as 7 μm onto the back surface of a card obtained by the same procedure as in Example 109, followed by drying, to obtain an information recording card.

All over the reversible recording portion of the obtained card, a color was developed by the use of a thermal head, and the recording portion was then pressed by a hot iron at 100° C. for 1 second and at this time, the color disappeared. Next, this operation was repeated several hundred times whereby a good coloring state and a good color disappearance state could be obtained.

COMPARATIVE EXAMPLE 8

Each mixture having the following composition was milled for 2 hours by a sand mill to obtain dispersions H, I and J.

| Dispersion H (color former dispersion) | |
| --- | --- |
| 2-anilino-3-methyl-6-di-n-buylaminofluoran | 2 parts |
| 10% aqueous polyvinyl alcohol solution | 2 parts |
| Water | 1 part |
| Dispersion I (developer dispersion) | |
| Bisphenol A | 2 parts |
| 10% aqueous polyvinyl alcohol solution | 2 parts |
| Water | 1 part |
| Dispersion J (pigment dispersion) | |
| Light-duty calcium carbonate | 2 parts |
| 0.7% aqueous sodium hexametaphosphate solution | 3 parts |

Heat-sensitive Coating Solution

One part of the solution H, 3 parts of the solution I and 5 parts of the solution J were sufficiently mixed, thereby obtaining a heat-sensitive coating solution.

This heat-sensitive coating solution was applied onto a polyethylene terephthalate film having a thickness of 100 μm so that the amount of the coating solution might be 5 g/m² in terms of dry weight, followed by drying, to obtain an information recording card.

(Evaluation)

All over the information recording cards obtained in Example 109 and Comparative Example 8, a color was developed at an application voltage of 24 V and an application energy of 0.43 mj/dot by the use of a thermal printer (TH-PMD, made by Ohkura Electric Co., Ltd.) to carry out the tests of light resistance, moist heat resistance and plasticizer resistance.

Furthermore, a bar code was printed on each recording card by the use of a bar-code printer (DPS 6000 Jr, made by Teraoka Seiko Co., Ltd.), and it was inspected whether or not a wavelength of 880 nm in a near infrared region could be read by the use of a bar-code inspector (Inspector III, made by RJS Co., Ltd.). The results are shown in Table 12.

The fastness of the color image was evaluated on the basis of a survival ratio represented by the following formula:

The survival ratio (%)={(the density of the color image after a test)/(the density of the color image before the test)}×100

The density was an OD value measured by the use of a Macbeth densitometer (TR-254 model) and an amber filter.

Test of Light Resistance (A in Table 12)

The light resistance was denoted by the survival ratio after the color image was irradiated with an ultraviolet carbon arc (made by Suga Test Machine Co., Ltd.) for 24 hours.

Test of Moist Heat Resistance (B in Table 12)

After the color image was maintained at 60° C. and a relative humidity of 90% for 24 hours, the density was measured to obtain the survival ratio.

Test of Plasticizer Stability (C in Table 12)

High-wrap (trade name, made by Mitsui Toatsu Chemicals, Inc.) was brought into contact with the color image, and a load of 100 g/cm$^2$ was then applied thereto. After the application of this load was maintained at 40° C. for 24 hours, the density was measured to obtain the survival ratio.

TABLE 12

| | Image stability (survival ratio: %) | | | |
| --- | --- | --- | --- | --- |
| | A | B | C | Readability of IR |
| Ex. 109 | 100 | 100 | 100 | Able |
| Comp. 8 | 12 | 84 | 14 | Unable |

As is apparent from Tables 6, 9, 11 and 12, heat-sensitive recording materials using carboxylates of the present invention are excellent in the stability of color images. In addition, as is apparent from FIGS. 3 to 6 and Table 12, absorption is possible even in a near infrared region, and so the application of these heat-sensitive recording materials to many uses can be expected.

What is claimed is:

1. A heat-sensitive recording material which comprises a support and a heat-sensitive recording layer on the support, said heat-sensitive recording layer containing at least one carboxylate represented by formula (1) or (2)

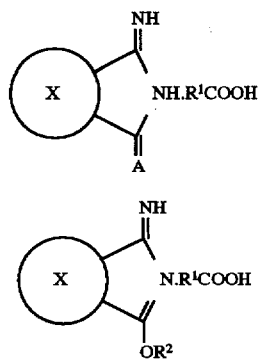

wherein a ring X is an unsubstituted aromatic residue or an aromatic residue substituted with a halogen atom, alkyl group, alkoxy group, aryloxy group, alkylcarbonyl group, arylcarbonyl group, alkylthio group, arylthio group, nitro group, dialkylamino group, amino group, alkylsilyl group, alkylsilyloxy group or trifluoromethyl group; A is =NH or (—OR$^3$ and —OR$^4$)(wherein each of R$^3$ and R$^4$ is independently an alkyl group having 1 to 8 carbon atoms which is unsubstituted or substituted with an allyloxy group or hydroxy group, and R$^3$ and R$^4$ may bond to each other to form a ring); R$^1$ is a hydrogen atom, an alkyl group having 1 to 20 carbon atoms which is unsubstituted or substituted with a halogen atom, hydroxy group, alkoxy group having 1 to 4 carbon atoms, aryloxy group, alkylthio group having 1 to 4 carbon atoms, alkoxycarbonyl group having 2 to 20 carbon atoms, amino group or amide group, an aralkyl group which is unsubstituted or substituted with a halogen atom, hydroxy group, alkyl group having 1 to 4 carbon atoms, alkoxy group having 1 to 4 carbon atoms, alkylthio group having 1 to 4 carbon atoms, amino group, carboxyl group, acyl group or nitro group, or an aryl group which is unsubstituted or substituted with a halogen atom, hydroxy group, alkyl group having 1 to 4 carbon atoms, alkoxy group having 1 to 4 carbon atoms, alkylthio group having 1 to 4 carbon atoms, amino group, carboxyl group, acyl group or nitro group, but when A is =NH, R$^1$ is a residue of benzoic acid, chlorobenzoic acid, hydroxybenzoic acid, anisic acid, toluic acid or nitrobenzoic acid; and R$^2$ is an alkyl group having 1 to 8 carbon atoms which is unsubstituted or substituted with an allyloxy group or hydroxy group.

2. The heat-sensitive recording material according to claim 1 wherein an adhesive layer and a release sheet are attached to the back surface of the support.

3. The heat-sensitive recording material according to claim 1 wherein a reversible recording layer is formed on the support.

4. The heat-sensitive recording material according to claim 3 wherein said reversible recording layer is a magnetic recording layer.

5. The heat-sensitive recording material according to claim 3 wherein said reversible recording layer is a cloudy recording layer.

6. The heat-sensitive recording material according to claim 3 wherein said reversible recording layer is a heat-sensitive recording layer comprising a leuco-dye and a developer.

7. The heat-sensitive recording material according to claim 1, wherein ring X is a benzene ring which is unsubstituted or substituted with a halogen atom, alkyl group having 1 to 8 carbon atoms, alkoxy group having 1 to 8 carbon atoms or nitro group, naphthalene ring which is unsubstituted or substituted with a halogen atom, alkyl group having 1 to 8 carbon atoms, alkoxy group having 1 to 8 carbon atoms or nitro group, or pyrazine ring which is unsubstituted or substituted with a halogen atom, alkyl group having 1 to 8 carbon atoms, alkoxy group having 1 to 8 carbon atoms or nitro group.

8. The heat-sensitive recording material according to claim 1, wherein R$^1$ is an alkyl group having 1 to 20 carbon atoms which is unsubstituted or substituted with an alkoxy group having 1 to 4 carbon atoms or alkoxycarbonyl group having 2 to 20 carbon atoms, or aryl groups which are unsubstituted or substituted with a chlorine atom, hydroxy group, alkyl group having 1 to 4 carbon atoms, alkoxy group having 1 to 4 carbon atoms, amino group or nitro group.

9. A heat-sensitive recording material which comprises a support and a heat-sensitive recording layer on the support, said heat-sensitive recording layer containing at least one carboxylate represented by formula (1) or (2) and at least one carbonyl compound having a hydrogen atom at an α-position and/or at least one aromatic isocyanate compound:

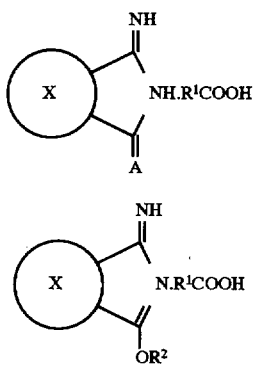

wherein a ring X is an unsubstituted aromatic residue or an aromatic residue substituted with a halogen atom, alkyl group, alkoxy group, aryloxy group, alkylcarbonyl group, arylcarbonyl group, alkylthio group, arylthio group, nitro group, dialkylamino group, amino group, alkylsilyl group, alkylsilyloxy group or trifluoromethyl group; A is =NH or (—OR$^3$ and —OR$^4$)(wherein each of R$^3$ and R$^4$ is independently an alkyl group having 1 to 8 carbon atoms which is unsubstituted or substituted with an allyloxy group or hydroxy group, and R$^3$ and R$^4$ may bond to each other to form a ring); R$^1$ is a hydrogen atom, an alkyl group having 1 to 20 carbon atoms which is unsubstituted or substituted with a halogen atom, hydroxy group, alkoxy group having 1 to 4 carbon atoms, aryloxy group, alkylthio group having 1 to 4 carbon atoms, alkoxycarbonyl group having 2 to 20 carbon atoms, amino group or amide group, an aralkyl group which is unsubstituted or substituted with a halogen atom, hydroxy group, alkyl group having 1 to 4 carbon atoms, alkoxy group having 1 to 4 carbon atoms, alkylthio group having 1 to 4 carbon atoms, amino group, carboxyl group, acyl group or nitro group, or an aryl group which is unsubstituted or substituted with a halogen atom, hydroxy group, alkyl group having 1 to 4 carbon atoms, alkoxy group having 1 to 4 carbon atoms, alkylthio group having 1 to 4 carbon atoms, amino group, carboxyl group, acyl group or nitro group; and R$^2$ iS an alkyl group having 1 to 8 carbon atoms which is unsubstituted or substituted with an allyloxy group or hydroxy group.

10. The heat-sensitive recording material according to claim 9 wherein an adhesive layer and a release sheet are attached to the back surface of the support.

11. The heat-sensitive recording material according to claim 9 wherein a reversible recording layer is formed on the support.

12. The heat-sensitive recording material according to claim 11 wherein said reversible recording layer is a magnetic recording layer.

13. The heat-sensitive recording material according to claim 11 wherein said reversible recording layer is a cloudy recording layer.

14. The heat-sensitive recording material according to claim 11 wherein said reversible recording layer is a heat-sensitive recording layer comprising a leuco-dye and a developer.

15. The heat-sensitive recording material according to claim 9, wherein ring X is a benzene ring which is unsubstituted or substituted with a halogen atom, alkyl group having 1 to 8 carbon atoms, alkoxy group having 1 to 8 carbon atoms or nitro group, naphthalene ring which is unsubstituted or substituted with a halogen atom, alkyl group having 1 to 8 carbon atoms, alkoxy group having 1 to 8 carbon atoms or nitro group, or pyrazine ring which is unsubstituted or substituted with a halogen atom, alkyl group having 1 to 8 carbon atoms, alkoxy group having 1 to 8 carbon atoms or nitro group.

16. The heat-sensitive recording material according to claim 9, wherein R$^1$ is an alkyl group having 1 to 20 carbon atoms which is unsubstituted or substituted with an alkoxy group having 1 to 4 carbon atoms or alkoxycarbonyl group having 2 to 20 carbon atoms, or aryl groups which are unsubstituted or substituted with a chlorine atom, hydroxy group, alkyl group having 1 to 4 carbon atoms, alkoxy group having 1 to 4 carbon atoms, amino group or nitro group.

* * * * *